United States Patent [19]
Alfano et al.

[11] Patent Number: 6,006,001
[45] Date of Patent: Dec. 21, 1999

[54] FIBEROPTIC ASSEMBLY USEFUL IN OPTICAL SPECTROSCOPY

[75] Inventors: Robert R. Alfano, Bronx; Stavros G. Demos, New York, both of N.Y.; Gang Zhang, Edison, N.J.

[73] Assignee: The Research Foundation of Cuny, New York, N.Y.

[21] Appl. No.: 08/982,332

[22] Filed: Dec. 2, 1997

Related U.S. Application Data

[60] Provisional application No. 60/032,233, Dec. 2, 1996, and provisional application No. 60/037,524, Feb. 10, 1997.

[51] Int. Cl.[6] .................................................. G02B 6/04
[52] U.S. Cl. ............................................................ 385/115
[58] Field of Search ................................. 600/200, 109, 600/129, 476, 477, 478, 475, 104, 113, 172; 250/339.12, 341.5; 356/301; 385/117

[56] References Cited

U.S. PATENT DOCUMENTS

| | | | |
|---|---|---|---|
| 4,964,692 | 10/1990 | Prscott ................................. | 385/117 |
| 5,261,410 | 11/1993 | Alfano et al. .......................... | 128/664 |
| 5,456,245 | 10/1995 | Bornhop et al. ....................... | 600/139 |
| 5,630,788 | 5/1997 | Forkner et al. ........................ | 600/182 |
| 5,667,473 | 9/1997 | Finn et al. ............................. | 600/104 |

*Primary Examiner*—Akm E. Ullah
*Attorney, Agent, or Firm*—Kriegsman & Kriegsman

[57] ABSTRACT

A fiberoptic assembly for optical spectroscopic analysis of a sample. In a preferred embodiment, the assembly is well-suited for use inside the working channel of an endoscope and comprises a tubular outer jacket and a tubular inner jacket, the inner jacket being coaxial with and positioned inside the outer jacket. The open front end of the inner jacket is spaced rearwardly a short distance relative to the open front end of the outer jacket. The outer jacket has an outer diameter of approximately 2.2 mm. The assembly also includes a plug made of fused silica. The plug has a front cylindrical portion of comparatively large cross-sectional diameter and a rear cylindrical portion of comparatively small cross-sectional diameter. The front portion is mounted within the outer jacket by a friction-fit and extends longitudinally from the open front end thereof to the open front end of the inner jacket. The rear portion of the plug is mounted within the inner jacket by a friction-fit and extends rearwardly from its open front end for a short distance. A narrow-band filter in the form of a dielectric-coating is formed on the rear end of the rear portion of the plug. The assembly also includes an illumination fiber centered within the inner jacket and spaced rearwardly a short distance from the narrow-band filter. The output end of the illumination filter is shaped to collimate light emergent therefrom. The assembly additionally comprises a plurality of light collection fibers, which fibers are disposed within the outer tubular jacket and are spaced about the outside of the inner tubular jacket.

39 Claims, 34 Drawing Sheets

FIBEROPTIC ASSEMBLY USEFUL IN OPTICAL SPECTROSCOPY

CROSS-REFERENCE TO RELATED APPLICATIONS

The present application claims the benefit under 35 U.S.C. 119(e) of U.S. Provisional Patent Application Ser. No. 60/032,233, filed Dec. 2, 1996, and U.S. Provisional Patent Application Ser. No. 60/037,524 filed Feb. 10, 1997, both of which are incorporated herein by reference.

BACKGROUND OF THE INVENTION

The present invention relates generally to the field of optical spectroscopy and more particularly to the use of optical spectroscopy to observe, analyze and/or characterize biological materials.

The use of optical spectroscopy as a tool for the in vivo and/or in vitro analysis of biological tissues and materials has been studied extensively over approximately the last ten years. This work has demonstrated that optical spectroscopy can be used to provide useful information about both the chemical composition and the morphological structure of biological tissues and materials. Fluorescence spectroscopy and elastic scattering are two of the most common types of optical spectroscopy techniques used to study biological materials. In fluorescence spectroscopy, the photoexcitation of molecules present in a tissue being examined is used to cause the tissue to emit a fluorescence signal that is characteristic of a particular tissue state, e.g., normal vs. benign tumor vs. malignant tumor, etc. In the case of elastic scattering, the absorption and scattering effects that a sample tissue exhibits to illumination provide information that can be used to discern the structure and makeup of the sample. Both of the aforementioned techniques provide a good signal-to-noise ratio for short exposure times to the illuminating light.

An example of fluorescence spectroscopy is disclosed in U.S. Pat. No. 5,131,398, inventors Alfano et al., which issued Jul. 21, 1992, and which is incorporated herein by reference. More specifically, the aforementioned patent describes a method and apparatus for distinguishing cancerous tumors and tissue from benign tumors and tissue or normal tissue using native fluorescence. The tissue to be examined is excited with a beam of monochromatic light at 300 nm. The intensity of the native fluorescence emitted from the tissue is measured at 340 and 440 nm. The ratio of the two intensities is then calculated and used as a basis for determining if the tissue is cancerous as opposed to being benign or normal. The method and apparatus are based on the discovery that, when tissue is excited with monochromatic light at 300 nm, the native fluorescence spectrum over the region from about 320 nm to 600 nm is substantially different for cancerous tissue than for either benign or normal tissue.

Still another type of optical spectroscopy that has been used to study biological materials is Raman spectroscopy. Raman spectroscopy, which arises from inelastic scattering of molecules within a sample, results in the generation of a Raman spectrum, said Raman spectrum containing one or more spectrally narrow peaks. These peaks can be used to identify large biological molecules within the sample or, in some cases, to identify the composition of complex, multi-component samples. Recently, the use of Raman spectroscopy in the study and diagnosis of diseased tissues has been shown.

For example, in U.S. Pat. No. 5,261,410, inventors Alfano et al., which issued Nov. 16, 1993, and which is incorporated herein by reference, there is disclosed a method for determining if a tissue is a malignant tumor tissue, a benign tumor tissue, or a normal or benign tissue using Raman spectroscopy. Said method is based on the discovery that, when irradiated with a beam of infrared, monochromatic light, malignant tumor tissue, benign tumor tissue, and normal or benign tissue produce distinguishable Raman spectra. For human breast tissue, some salient differences in the respective Raman spectra are the presence of four Raman bands at a Raman shift of about 1078, 1300, 1445 and 1651 $cm^{-1}$ for normal or benign tissue, the presence of three Raman bands at a Raman shift of about 1240, 1445 and 1659 $cm^{-1}$ for benign tumor tissue, and the presence of two Raman bands at a Raman shift of about 1445 and 1651 $cm^{-1}$ for malignant tumor tissue. The aforementioned patent also teaches that, for human breast tissue, the ratio of intensities of the Raman bands at a Raman shift of about 1445 and 1659 $cm^{-1}$ is about 1.25 for normal or benign tissue, about 0.93 for benign tumor tissue, and about 0.87 for malignant tumor tissue.

In addition to having applications of the type described above, Raman spectroscopy has also been suggested in recent reports to have the potential to be used in the study and diagnosis of the evolution of precancerous and cancerous lesions in human tissues in vivo.

The Raman scattering process is based on the inelastic scattering of light and typically generates an extremely weak signal, e.g., $10^{-6}$–$10^{-14} I_0$ where $I_0$ is the illuminating laser light intensity. The Raman spectrum comprises two spectral components, the Stokes spectrum and the antiStokes spectrum. The Stokes spectrum is located at longer wavelengths than the illuminating laser line whereas the antiStokes spectrum is located at shorter wavelengths than the illuminating laser line. For the above reasons, it can be appreciated that it is essential for Raman spectroscopy that the illuminating laser light be monochromatic and spectrally clean in order for the weak Raman signal emitted by the sample to be observable. At present, Raman spectroscopy is typically performed using a near infrared laser source (e.g., diode laser) and cooled silicon CCD detectors. In general, this type of arrangement yields an acceptable S/N ratio with relatively short integration times.

For Raman spectroscopy to be performed in vivo inside a body, fiberoptics must be used. However, as the illuminating light travels through an optic fiber to a tissue located inside a body, it is common for other spectral components to be generated in the illuminating light due to Raman scattering, fluorescence or like phenomena taking place within the fiber medium. The result of these phenomena is that the light exiting the fiber is not as spectrally clean as necessary. This problem becomes more severe as the length of the fiber increases. As shown in FIG. 1, one way to address this problem is to position a spectrograph, spectrometer or filter array after the fiber. Unfortunately, however, the physical size of these types of filtering arrangements is large (e.g., a few centimeters or larger) and precludes the use of these types of arrangements in many in vivo applications where the fiber is inserted into a working channel of an endoscope, said working channel typically having a diameter about 3 mm.

SUMMARY OF THE INVENTION

It is an object of the present invention to provide a fiberoptic assembly that overcomes at least some of the problems described above.

It is another object of the present invention to provide a fiberoptic assembly as described above that is well-suited for use in optical spectroscopy techniques.

It is another object of the present invention to provide a fiberoptic assembly as described above that is appropriately dimensioned for use in the working channel of an endoscope.

According to one aspect of the present invention, there is described a fiberoptic assembly, said fiberoptic assembly comprising (a) an illumination fiber, said illumination fiber having an output end; (b) a first light collection fiber, said first light collection fiber having an input end; (c) a tubular jacket, at least said output end of said illumination fiber and at least said input end of said first light collection fiber being disposed within said tubular jacket; and (d) a narrow band filter, said narrow band filter being aligned with and positioned after said output end of said illumination fiber and having a cross-sectional area no larger than that of said tubular jacket.

According to another aspect of the present invention, there is described a fiberoptic assembly, said fiber optic assembly comprising (a) an illumination fiber, said illumination fiber having an output end; (b) an inner tubular jacket, at least said output end of said illumination fiber being disposed within said inner tubular jacket; (c) an outer tubular jacket, said inner tubular jacket being coaxial with and disposed within said outer tubular jacket; (d) a plurality of light collection fibers, each of said light collection fibers having an input end, at least said output ends of said plurality of light collection fibers being disposed within said outer tubular jacket and spaced about the outside of said inner tubular jacket; and (e) a narrow band filter, said narrow band filter being aligned with and positioned after said output end of said illumination fiber and having a cross-sectional area no larger than that of said outer tubular jacket.

In a preferred embodiment, the fiberoptic assembly is well-suited for use inside the working channel of an endoscope and comprises a tubular outer jacket and a tubular inner jacket, the inner jacket being coaxial with and positioned inside the outer jacket. The open front end of the inner jacket is spaced rearwardly a short distance relative to the open front end of the outer jacket. The outer jacket has an outer diameter of approximately 2.2 mm. The assembly also includes a plug made of fused silica. The plug has a front cylindrical portion of comparatively large cross-sectional diameter and a rear cylindrical portion of comparatively small cross-sectional diameter. The front portion is mounted within the outer jacket by a friction-fit and extends longitudinally from the open front end thereof to the open front end of the inner jacket. The rear portion of the plug is mounted within the inner jacket by a friction-fit and extends rearwardly from its open front end for a short distance. A narrow-band filter in the form of a dielectric-coating is formed on the rear end of the rear portion of the plug. The assembly also includes an illumination fiber centered within the inner jacket and spaced rearwardly a short distance from the narrow-band filter. The output end of the illumination filter is shaped to collimate light emergent therefrom. The assembly additionally comprises a plurality of light collection fibers, which fibers are disposed within the outer tubular jacket and are spaced about the outside of the inner tubular jacket.

Additional objects, features, aspects and advantages of the present invention will be set forth, in part, in the description which follows and, in part, will be obvious from the description or may be learned by practice of the invention. In the description, reference is made to the accompanying drawings which form a part thereof and in which is shown by way of illustration specific embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate preferred embodiments of the invention and, together with the description, serve to explain the principles of the invention. In the drawings wherein like reference numerals represent like parts.

DETAILED DESCRIPTION OF PREFERRED EMBODIMENTS

Figure 1:
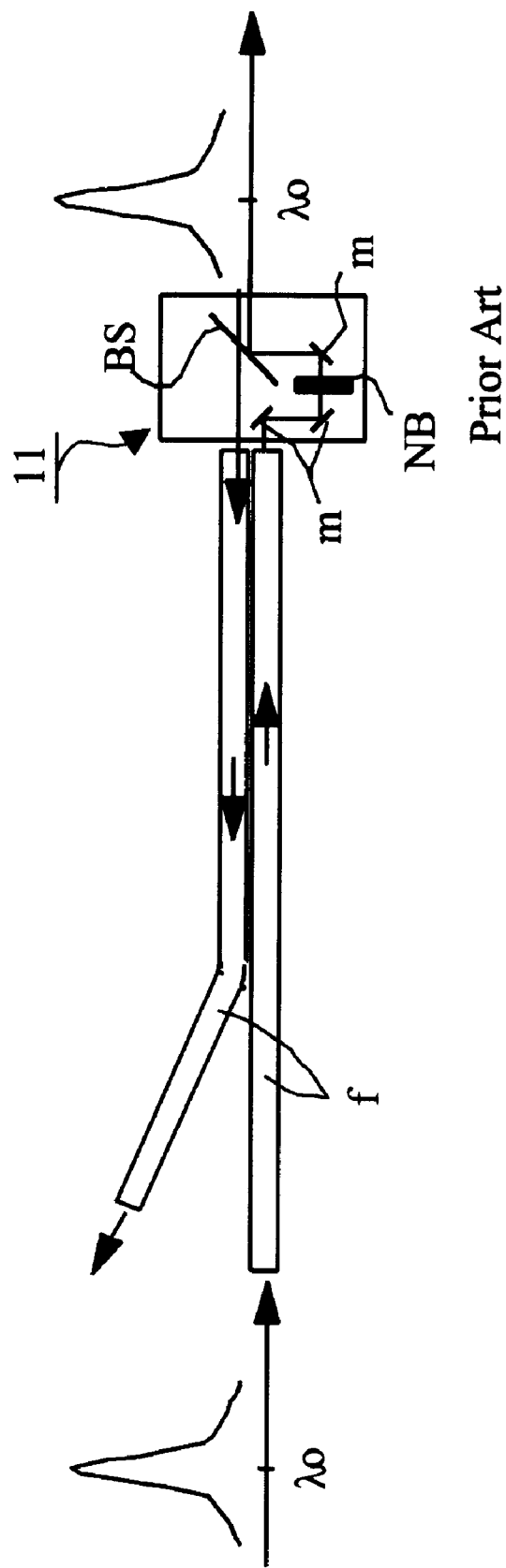
FIG. 1 is a schematic view of an existing approach to correcting spectral broadening of light propagating through an optic fiber.

As noted above, one problem encountered in using optical fibers in spectroscopic processes is that the light emergent from the fibers is often not spectrally clean. Referring now to FIG. 1, there is shown one type of prior art device for filtering the light emergent from an optical fiber f to address the aforementioned problem of spectral broadening, the prior art device being represented generally by reference numeral 11. As can be seen, device 11 comprises a plurality of mirrors m, a narrow band filter NB and a beam splitter BS. As pointed out above, one problem with device 11 is that it typically has a size on the order of 5 cm×5 cm, which precludes its use with fiberoptics used in vivo.

Figure 2:
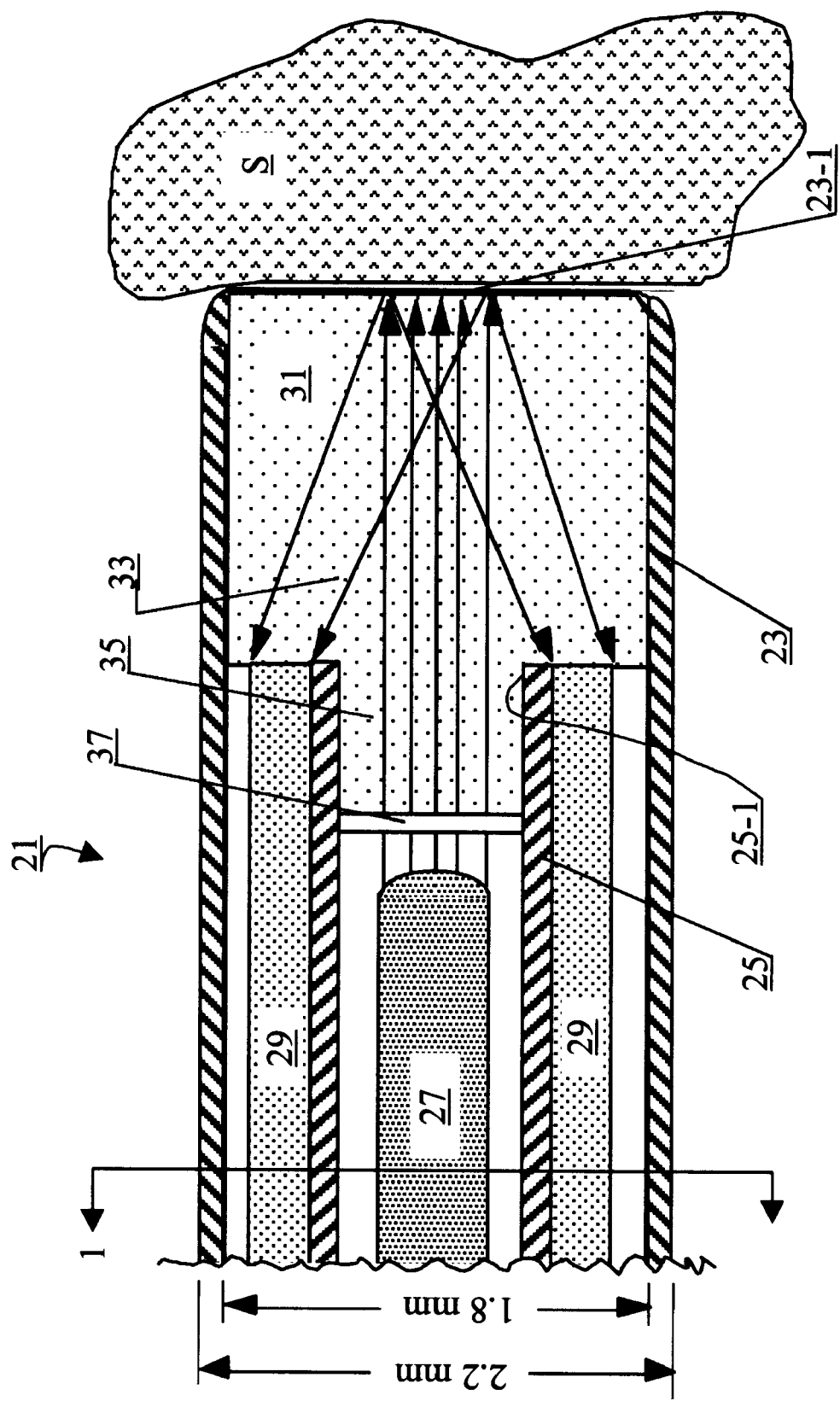
FIG. 2 is a fragmentary schematic longitudinal section view of a first embodiment of a fiberoptic assembly constructed according to the teachings of the present invention, the fiberoptic assembly being shown used to illuminate and collect light from a sample.

Referring now to FIG. 2, there is shown a fragmentary schematic longitudinal section view of a first embodiment of a fiberoptic assembly constructed according to the teachings of the present invention, the fiberoptic assembly being represented generally by reference numeral 21. For illustrative purposes, assembly 21 is shown being used to illuminate and collect light from a sample S.

Assembly 21 comprises a hollow, cylindrical, outer jacket 23 and a hollow, cylindrical, inner jacket 25, inner jacket 25 being coaxial with and positioned inside outer jacket 23. For reasons to become apparent below, inner jacket 25 has an open front end 25-1 that is spaced rearwardly relative to an open front end 23-1 provided in outer jacket 23. Outer jacket 23 and inner jacket 25 are both made of stainless steel or a similarly suitable material. Inner jacket 25 has a diameter of about 1 mm, and outer jacket 23 has an outer diameter of approximately 2.2 mm and an inner diameter of approximately 1.8 mm.

Assembly 21 further comprises a spacer or plug 31 made of fused silica, glass or a similarly suitable material for reducing stray light, plug 31 having a front cylindrical portion 33 of comparatively larger cross-sectional diameter and a rear cylindrical portion 35 of comparatively smaller cross-sectional diameter. Front cylindrical portion 33 is mounted within outer jacket 23 by a friction-fit and extends longitudinally from open end 25-1 of jacket 25 to open end 23-1 of outer jacket 23. Rear cylindrical portion 35 is mounted within inner jacket 25 by a friction-fit and extends rearwardly from open end 25-1 for a short distance. Plug 31 is intended to enable the tip of assembly 21 to be placed in contact with the sample being examined. Although plug 31 will cause an unwanted weak Raman signal to be generated, this signal can be subtracted-out from the recorded Raman spectrum as constituting a fixed, known background.

Assembly 21 further comprises a narrow-band filter 37 for filtering out undesired spectral components of light. In the present embodiment, filter 37 is in the form of a dielectric-coating (660 μm in diameter) formed on the rear end of plug 31. Instead of using filter 37, one could introduce appropriate refraction index variations inside the fiber forming a grating so that only the particular wavelength desired is transmitted.

Figure 3:
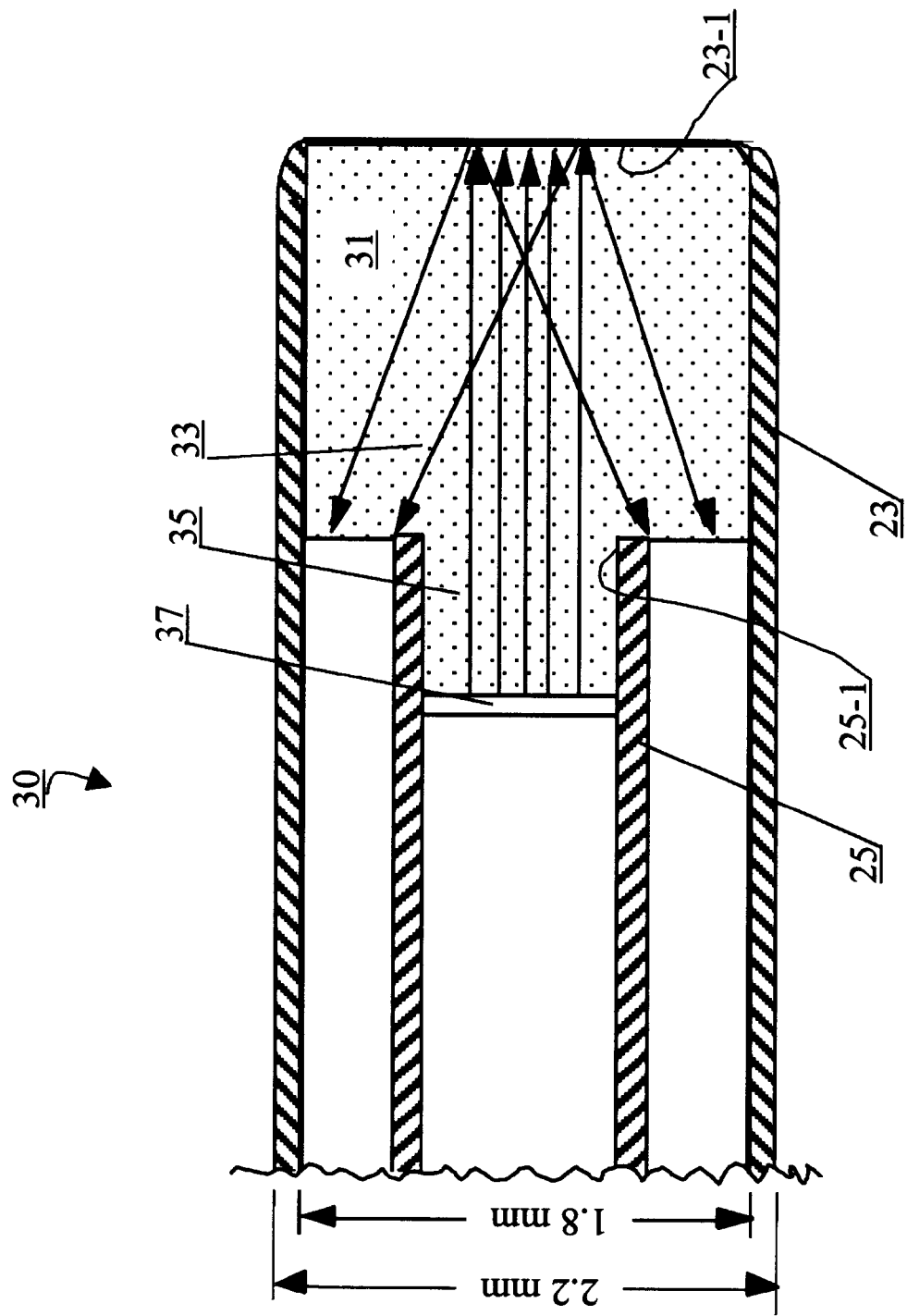
FIG. 3 is a fragmentary schematic longitudinal section view of the tip of the fiberoptic assembly of FIG. 2.

In the present embodiment, outer jacket 23, inner jacket 25, plug 31 and filter 37 together define a tip 30 (see FIG. 3), into which, as will hereinafter be described, the end of a fiberoptic bundle may be partially inserted.

Assembly 21 also comprises an illumination fiber 27, which fiber may be used to transmit illumination from a light source (not shown) to sample S in furtherance of an optical spectroscopy technique. In the present embodiment, fiber 27 has a diameter of approximately 50–400 μm and is centered within inner jacket 25.

Figure 4:
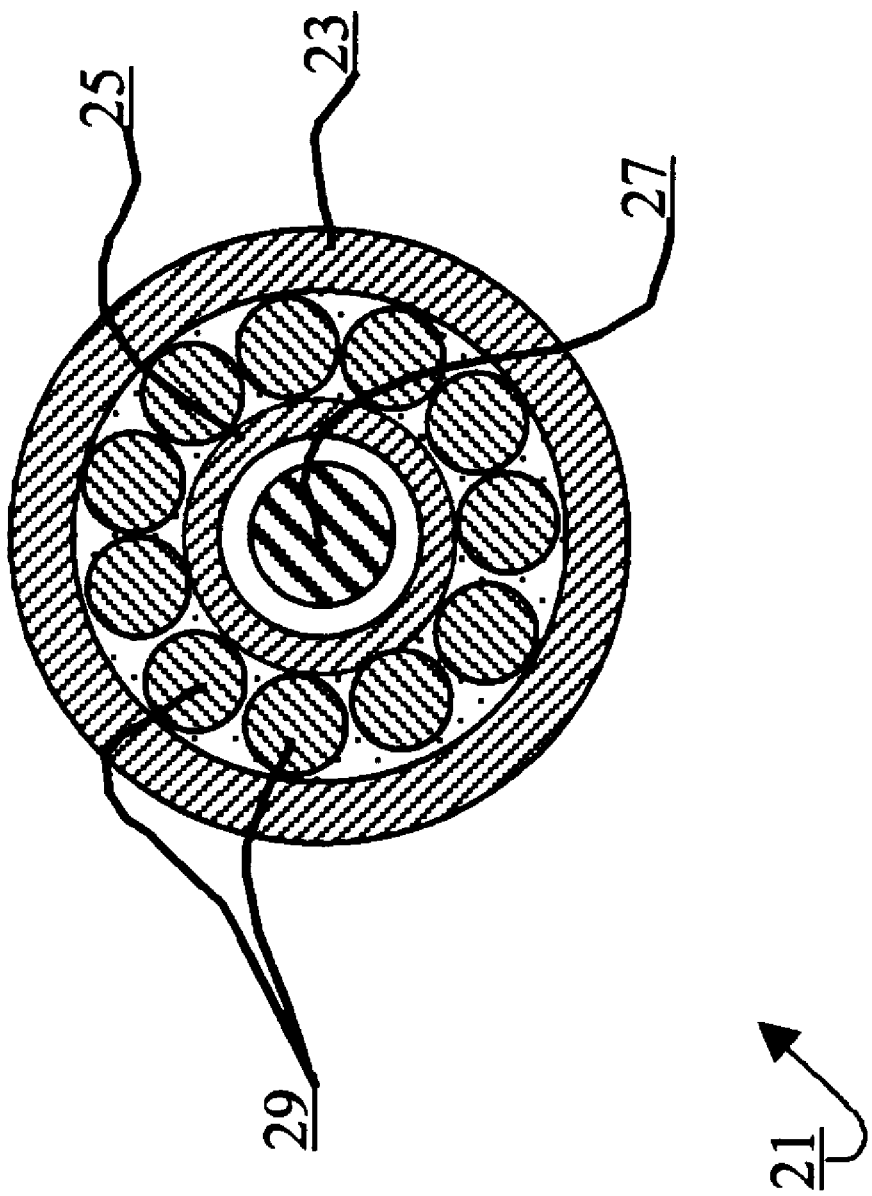
FIG. 4 is a schematic transverse section view of the fiberoptic assembly of FIG. 2 taken along line 1—1.

Assembly 21 additionally comprises a plurality of collection fibers 29, which fibers may be used to collect light from sample S and transmit said collected light to light detection and/or analysis means in furtherance of an optical spectroscopy technique. In the present embodiment, each of fibers 29 has a diameter of approximately 200 μm, the plurality of fibers 29 being distributed throughout jacket 23 so as to surround inner jacket 25 and, thus, illumination fiber 27 (see FIG. 4).

As can readily be appreciated, because of the compact size of tip 30 (its transverse cross-sectional diameter being less than 3 mm), assembly 21 is small enough to fit inside the working channel of an existing endoscope or inside the opening of a needle (see, for example, U.S. patent application Ser. No. 08/522,827, which is incorporated herein by reference, for applications of fiberoptics in needles). Moreover, because of the design of tip 30, assembly 21 can be used to touch the surface of the sample being examined so that easy and repeatable positioning is achievable and so that signals arising from media between the end of assembly 21 and the sample are avoided. Furthermore, except for the end of a fiberoptic bundle that is inserted into tip 30, the remainder of the fiberoptic bundle is flexible.

Assembly 21 is suitable for use in a variety of medical and non-medical applications and satisfies the above-described requirements for all types of optical spectroscopy, such as Raman scattering, resonance-Raman scattering, hot luminescence spectroscopy, fluorescence spectroscopy, plasma spectroscopy, atomic optical spectroscopy, etc.

Figure 5:
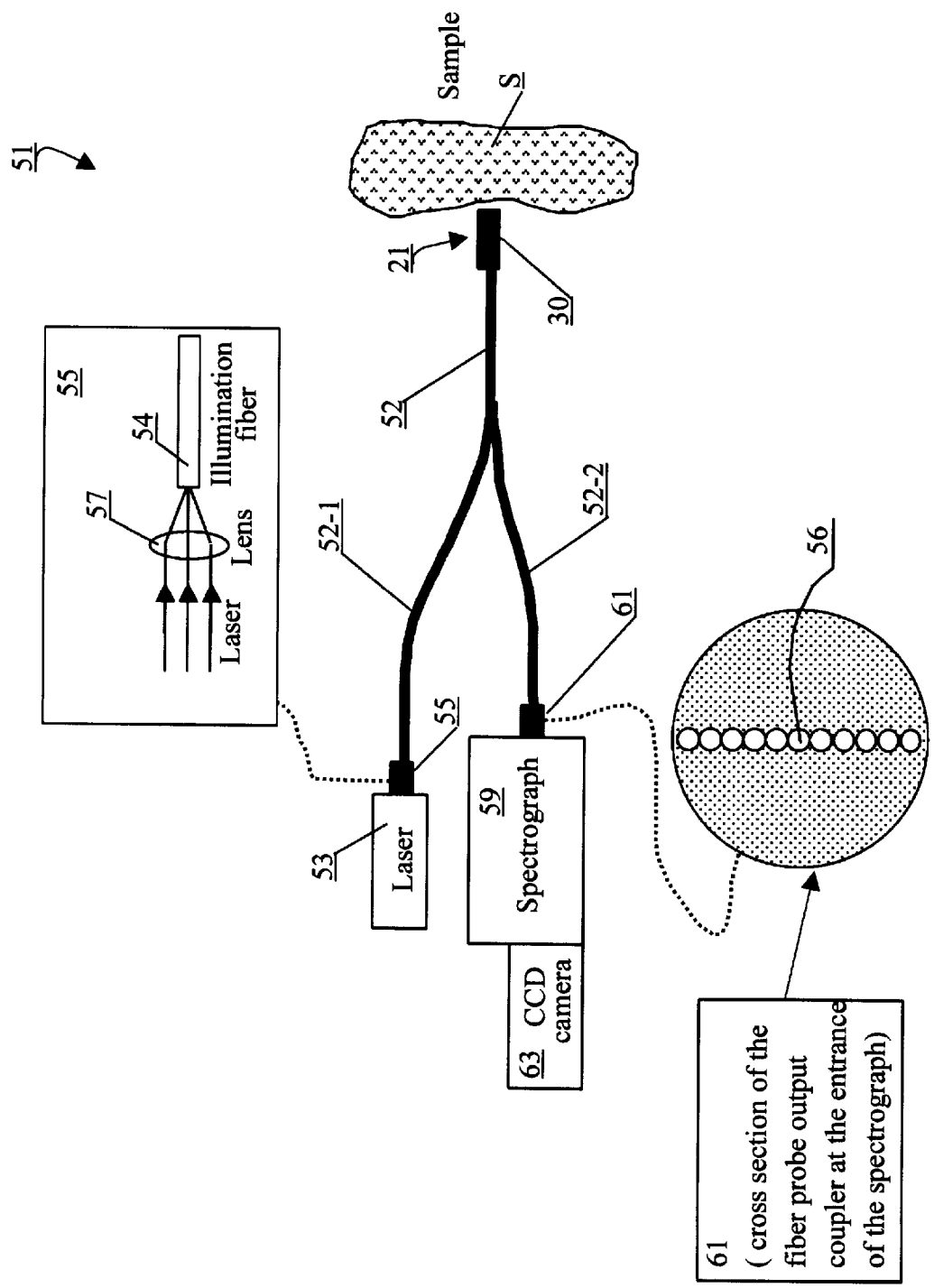
FIG. 5 is a schematic view of a first optical spectroscopy system for analyzing a sample, the optical spectroscopy system being constructed according to the teachings of the present invention.

Referring now to FIG. 5, there is shown a schematic view of a first optical spectroscopy system for analyzing a sample S, the optical spectroscopy system being constructed according to teachings of the present invention and being represented by reference numeral 51.

System 51 includes a laser 53. The particulars of laser 53 are preferably selected depending upon the application of system 51; for example, where system 51 is used for Raman analysis of biological materials, laser 53 may be a diode laser emitting at 800 nm.

System 51 also includes a fiberoptic bundle 52, bundle 52 comprising an illumination fiber 54 surrounded by a plurality of collection fibers 56. Bundle 52 is bifurcated at one end into a pair of legs 52-1 and 52-2. Leg 52-1 of bundle 52 is connected to laser 53 by a coupler 55, coupler 55 including a lens 57 for focusing the output of laser 53 onto fiber 54 of bundle 52. The end of bundle 52 opposite to legs 52-1 and 52-2 is partially inserted into a tip 30 to yield an assembly of the type shown in FIG. 2.

System 51 further includes a spectrograph 59 for spectral resolution of the light transmitted through leg 52-2, the input of spectrograph 59 being coupled to the output of leg 21-2 of probe 21 by a coupler 61. The output of spectrograph 59 is transmitted to a CCD camera 63 for detection of the spectral components resolved by spectrograph 59.

Figure 6:
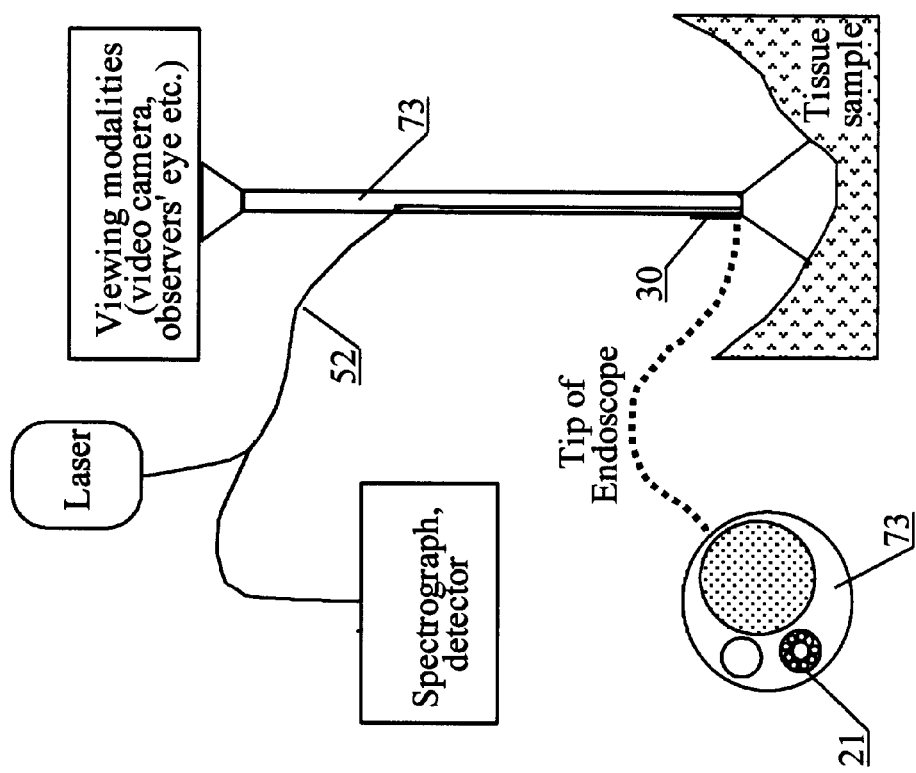
FIG. 6 is a schematic view of a second optical spectroscopy system for analyzing a sample, the optical spectroscopy system being constructed according to the teachings of the present invention.

Referring now to FIG. 6, there is shown a schematic view of a second optical spectroscopy system for analyzing a sample, the optical spectroscopy system being constructed according to the teachings of the present invention and being represented generally by reference numeral 71.

System 71 is similar to system 51, the principal difference between the two systems being that, in system 71, a portion of bundle 52 is placed inside the working channel of an endoscope 73 to enable a tip 30 also placed inside the working channel of the endoscope and mounted on the end of bundle 52 to reach certain parts of a body in vivo. Outside endoscope 73, system 71 is similar to system 51 in that the illuminating fiber of bundle 52 is coupled to a laser by a coupler (not shown) and in that the collection fibers of bundle are coupled to a spectrograph and detector by a coupler (not shown).

Figure 7:
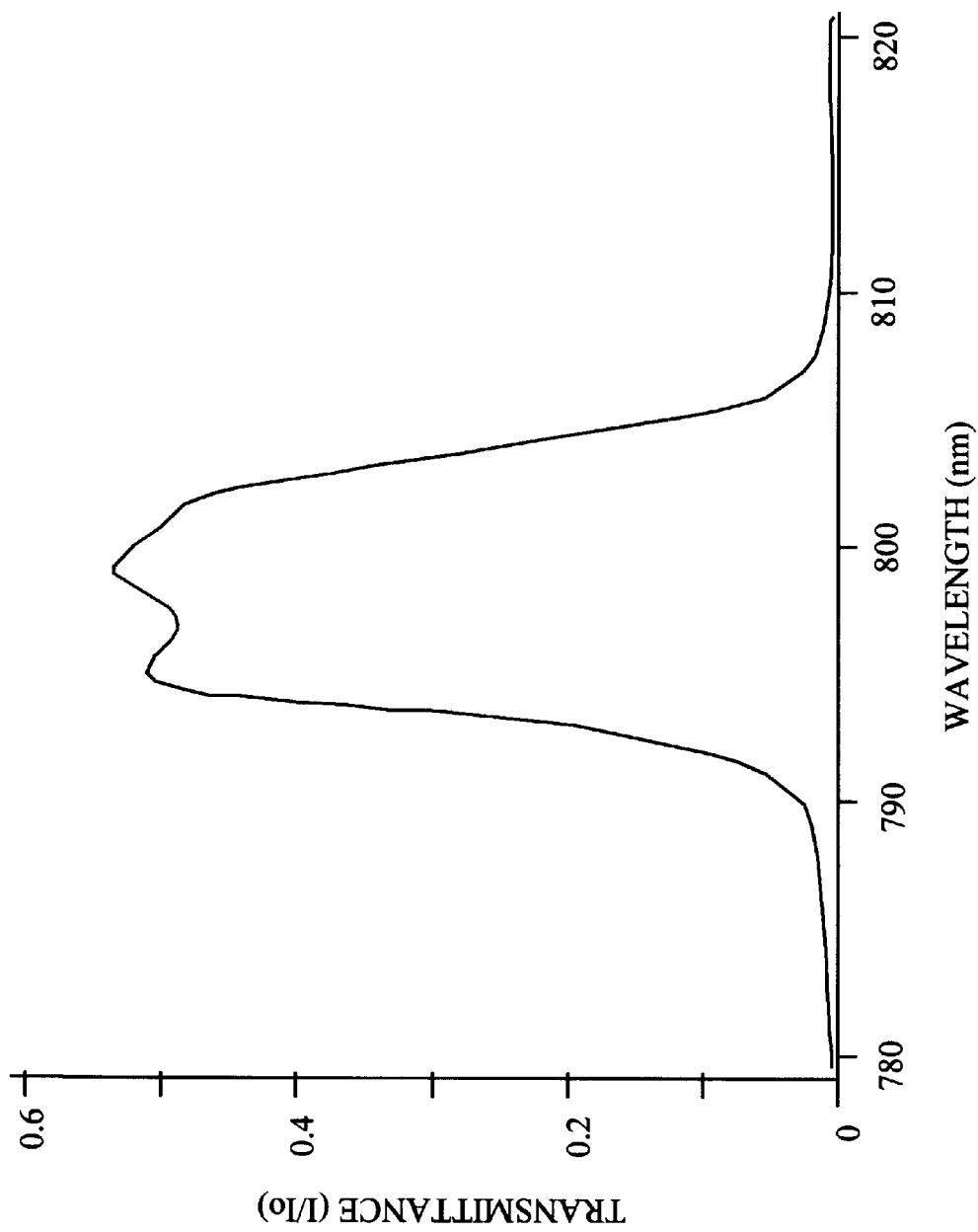
FIG. 7 is a graphic representation of the actual transmittance spectral profile of light from a diode laser emitting at 800 nm using an assembly such as that shown in FIG. 2.

Referring now to FIG. 7, there is shown a representation of the actual transmittance spectral profile of light from a diode laser emitting at 800 nm using an assembly such as assembly 21. As can be seen, the profile shown is indicative of the use of a typical narrow spectral band filter that allows for the transmission of the illuminating central wavelength while eliminating all other spectral components.

Figure 8:
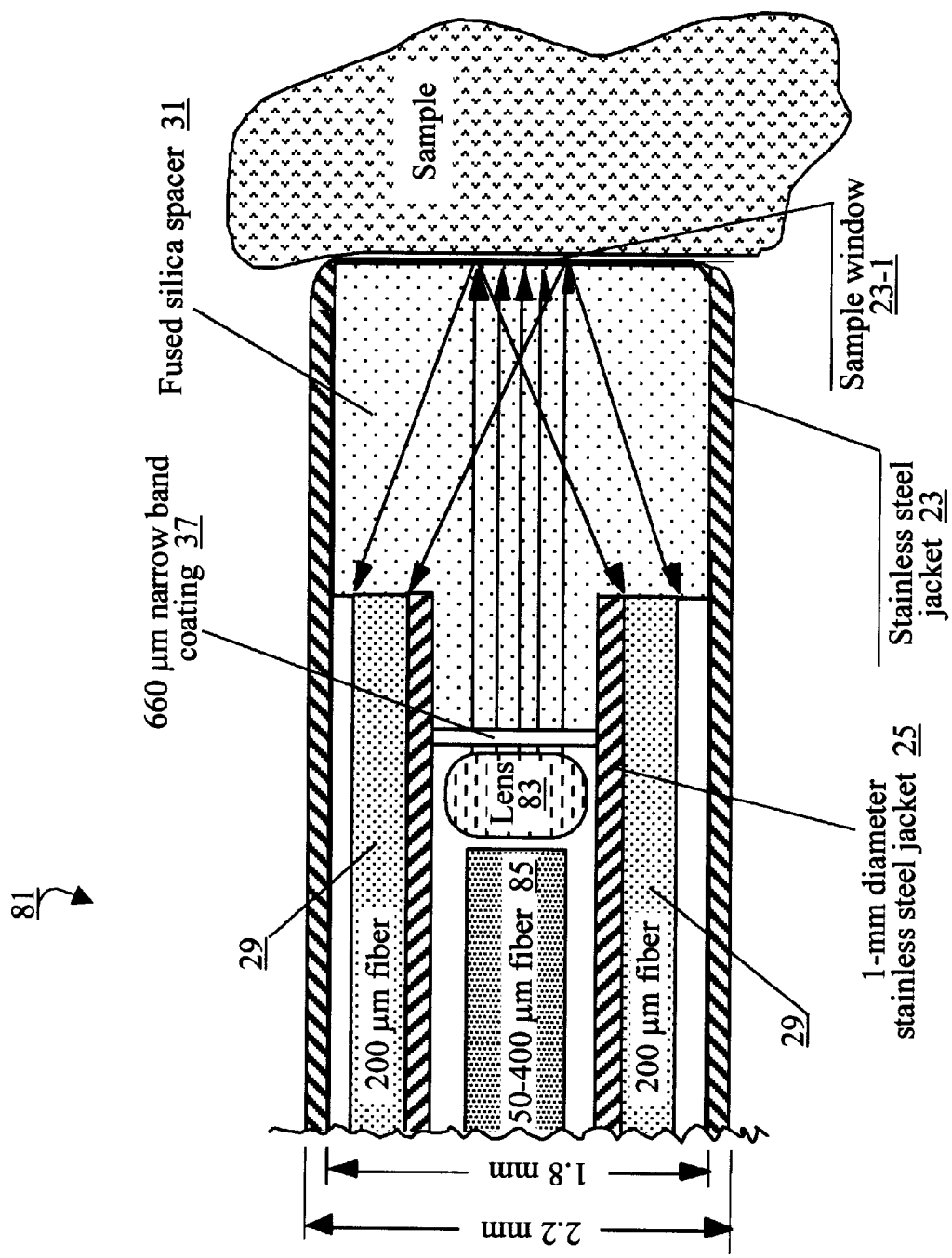
FIG. 8 is a fragmentary schematic longitudinal section view of a second embodiment of a fiberoptic assembly constructed according to the teachings of the present invention, the fiberoptic assembly being shown used to illuminate and collect light from a sample.

Referring now to FIG. 8, there is shown a fragmentary schematic view of a second embodiment of a fiberoptic assembly constructed according to the teachings of the present invention, the fiberoptic assembly being represented generally by reference numeral 81. For illustrative purposes, fiberoptic assembly 81 is shown being used to illuminate and collect light from a sample.

Assembly 81 is similar to assembly 21, the only differences between the two assemblies being that, in assembly 81, (i) an illumination fiber 85 having a flat output end is used and (ii) a lens 83 is placed inside jacket 25 between illumination fiber 85 and filter 37 so as to collimate the beam emergent from illumination fiber 85 whereas, in assembly 21, the output end of illumination fiber 27 is shaped to achieve a collimated beam directly from the fiber.

As a general matter, the optimal diameter of the illuminating fiber will typically be dependent upon how the output beam is collimated. If, as in the case of assembly 21, the illuminating fiber is shaped to collimate the beam emergent therefrom, then a larger diameter (about 400 μm) for the illuminating fiber is preferred. If, as in the case of assembly 81, a lens (microlens or self-focusing lens) is used for collimation, a smaller diameter (50–100 μm) for the illuminating fiber is preferred. The diameter of the collection fiber will generally be dependent upon the size of the assembly tip and the desired spectral resolution of the system. A larger diameter offers higher collection efficiency; however, when the fibers are coupled to the input of a spectrograph, a loss of spectral resolution is experienced. Although the collection fibers of assemblies 21 and 81 have a diameter of 200 μm, some variation from this diameter will likely be preferable, depending on the goals one wants to achieve, e.g., more light collection or higher spectral resolution.

Figure 9:
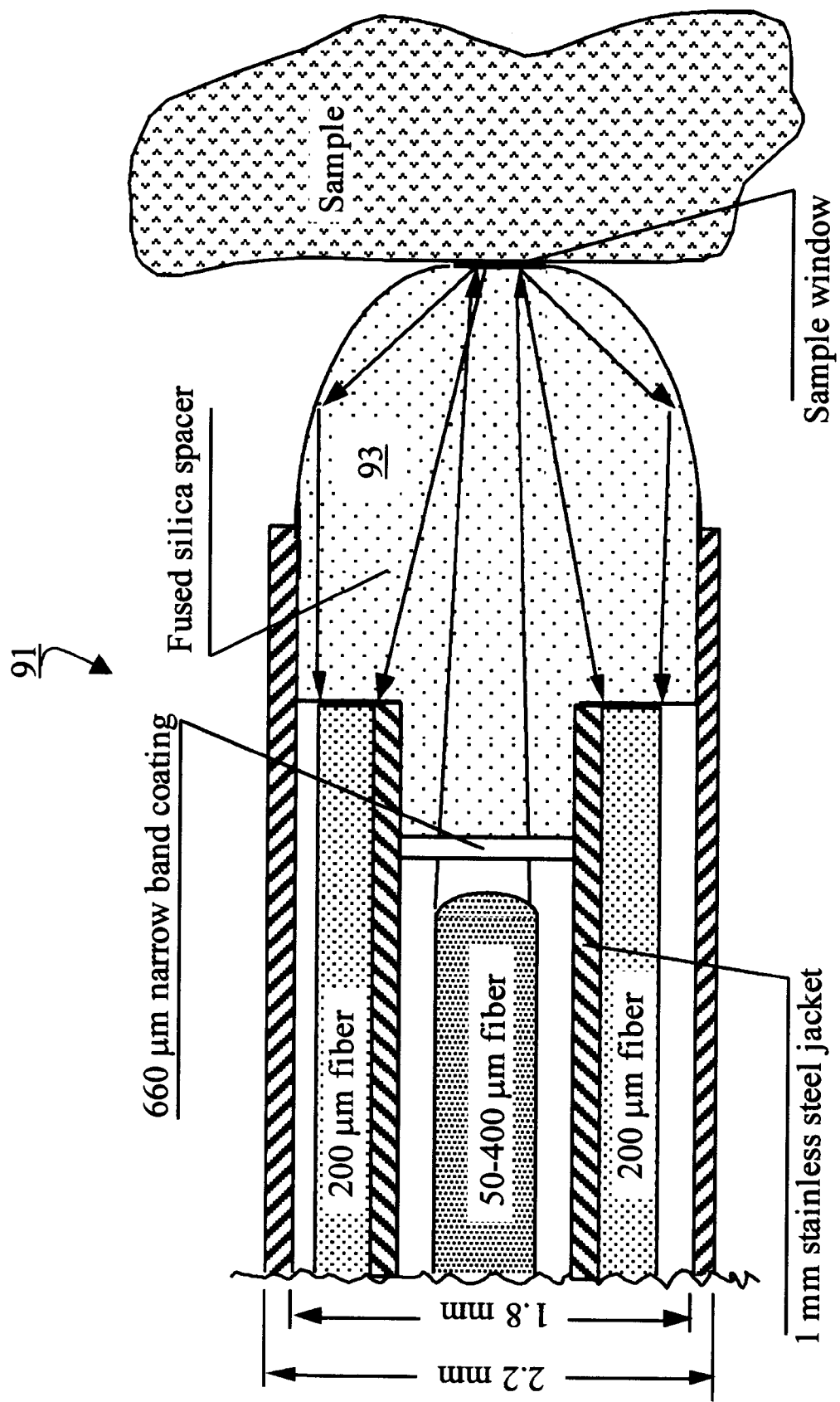
FIG. 9 is a fragmentary schematic longitudinal section view of a third embodiment of a fiberoptic assembly constructed according to the teachings of the present invention, the fiberoptic assembly being shown used to illuminate and collect light from a sample.
Figure 10:
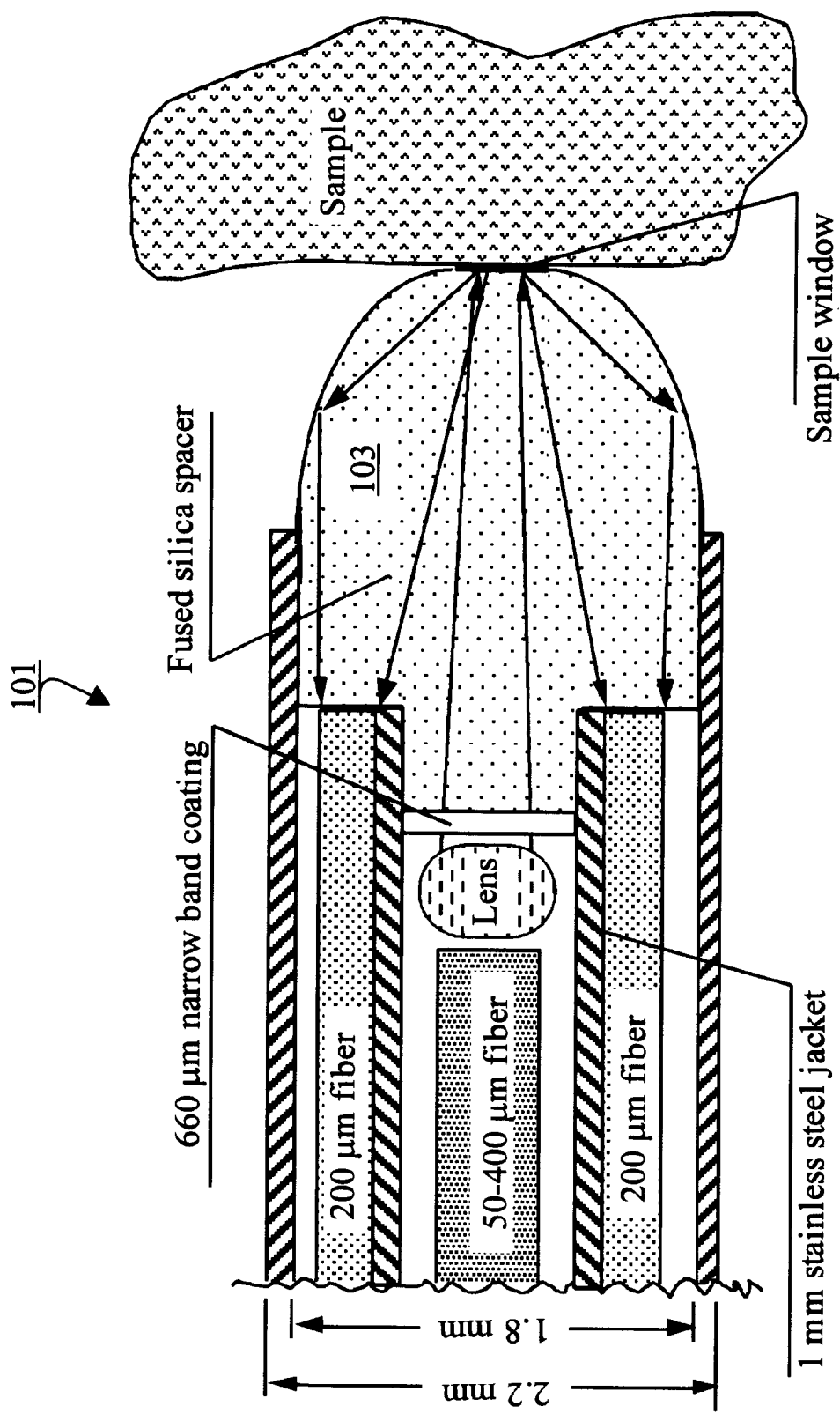
FIG. 10 is a fragmentary schematic longitudinal section view of a fourth embodiment of a fiberoptic assembly constructed according to the teachings of the present invention, the fiberoptic assembly being shown used to illuminate and collect light from a sample.

Certain shapes of the plug can increase the amount of light collected from the sample and thus improve the collection efficiency of the assembly. Referring now to FIGS. 9 and 10, there are shown assemblies 91 and 101, respectively. Assemblies 91 and 101 are identical to assemblies 21 and 81, respectively, except that assemblies 91 and 101 have spacers 93 and 103, respectively, whose front ends are in the shape of parabolas.

Figure 11:
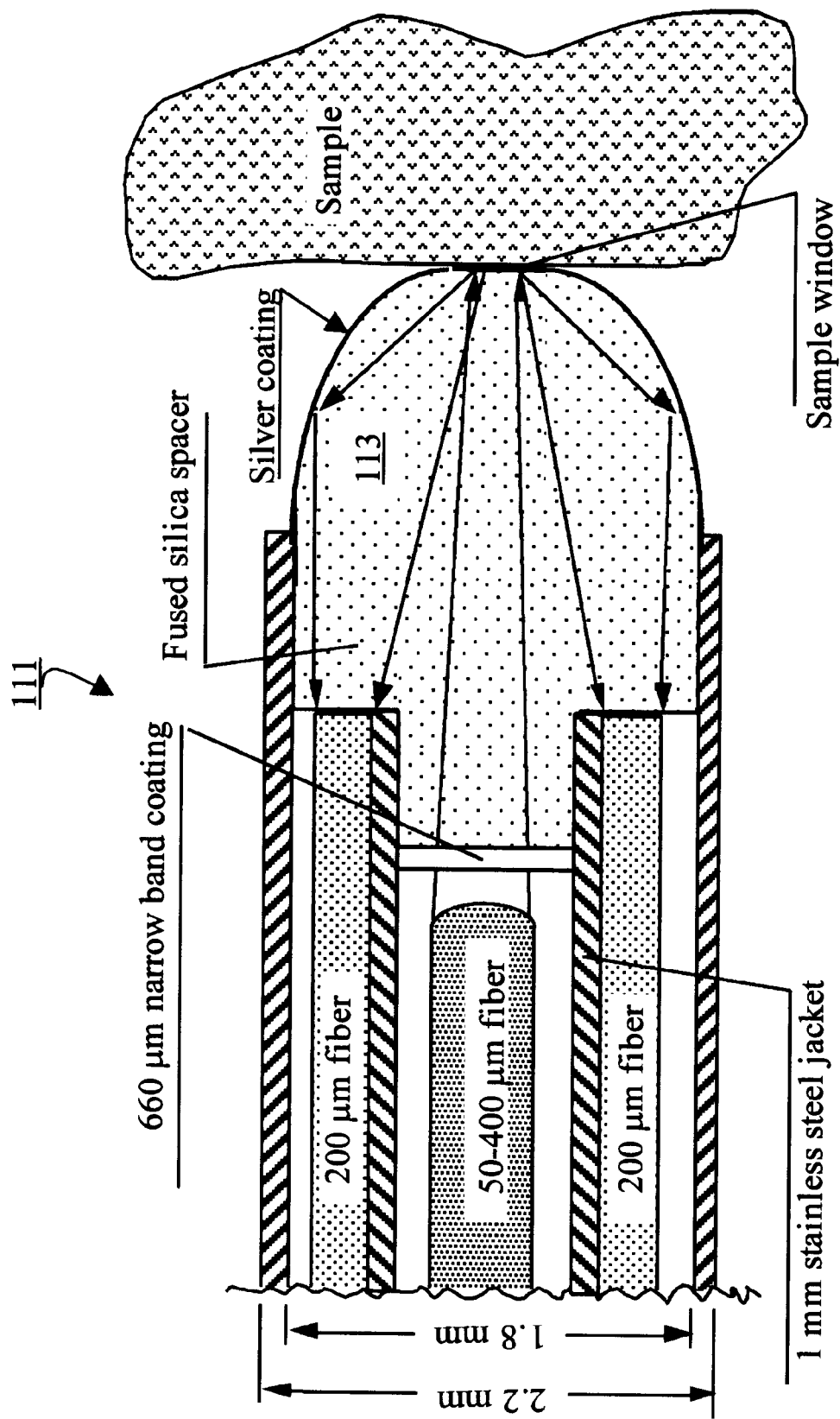
FIG. 11 is a fragmentary schematic longitudinal section view of a fifth embodiment of a fiberoptic assembly constructed according to the teachings of the present invention, the fiberoptic assembly being shown used to illuminate and collect light from a sample.
Figure 12:
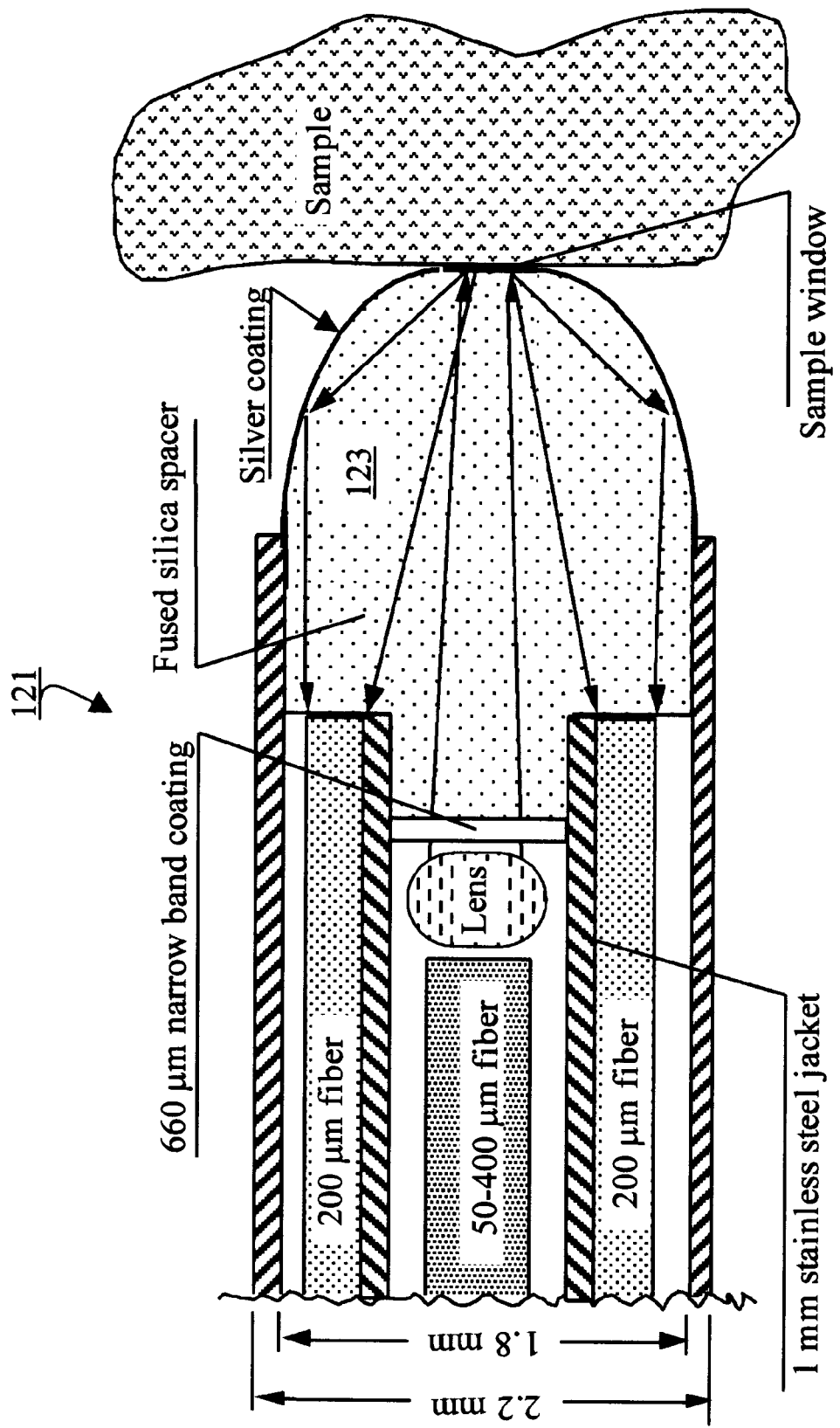
FIG. 12 is a fragmentary schematic longitudinal section view of a sixth embodiment of a fiberoptic assembly constructed according to the teachings of the present invention, the fiberoptic assembly being shown used to illuminate and collect light from a sample.
Figure 13:
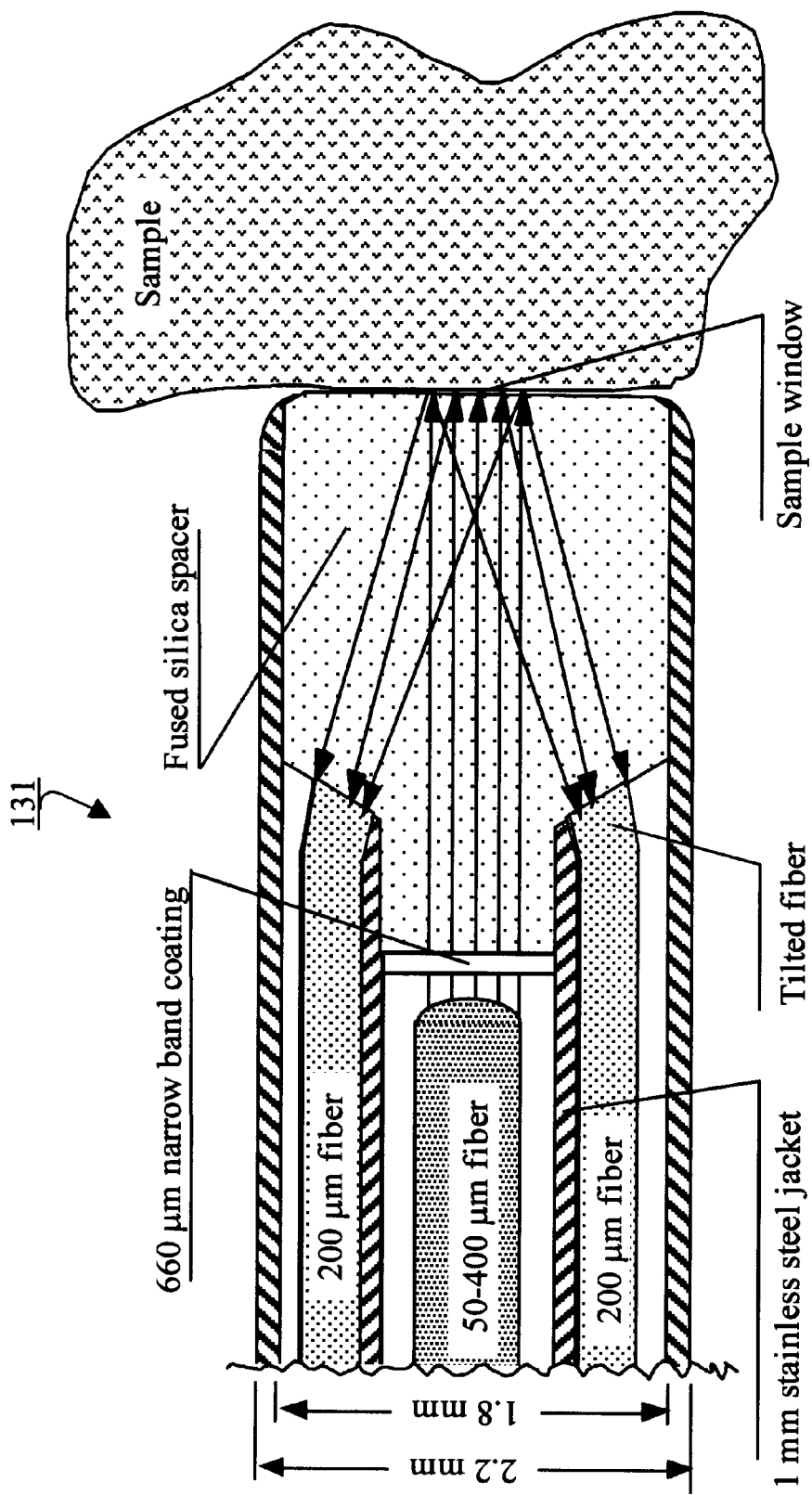
FIG. 13 is a fragmentary schematic longitudinal section view of a seventh embodiment of a fiberoptic assembly constructed according to the teachings of the present invention, the fiberoptic assembly being shown used to illuminate and collect light from a sample.
Figure 14:
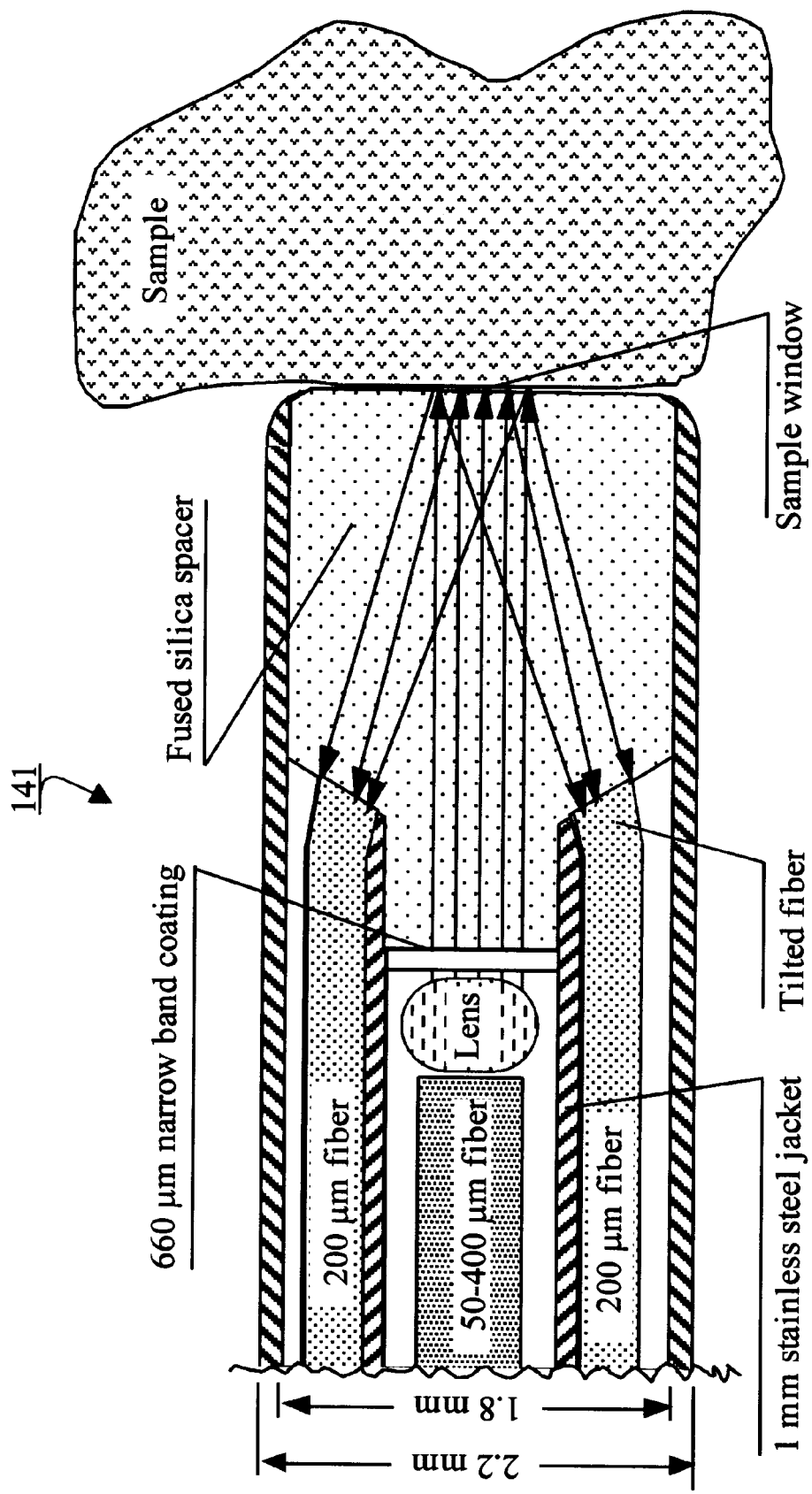
FIG. 14 is a fragmentary schematic longitudinal section view of a eighth embodiment of a fiberoptic assembly constructed according to the teachings of the present invention, the fiberoptic assembly being shown used to illuminate and collect light from a sample.
Figure 15:
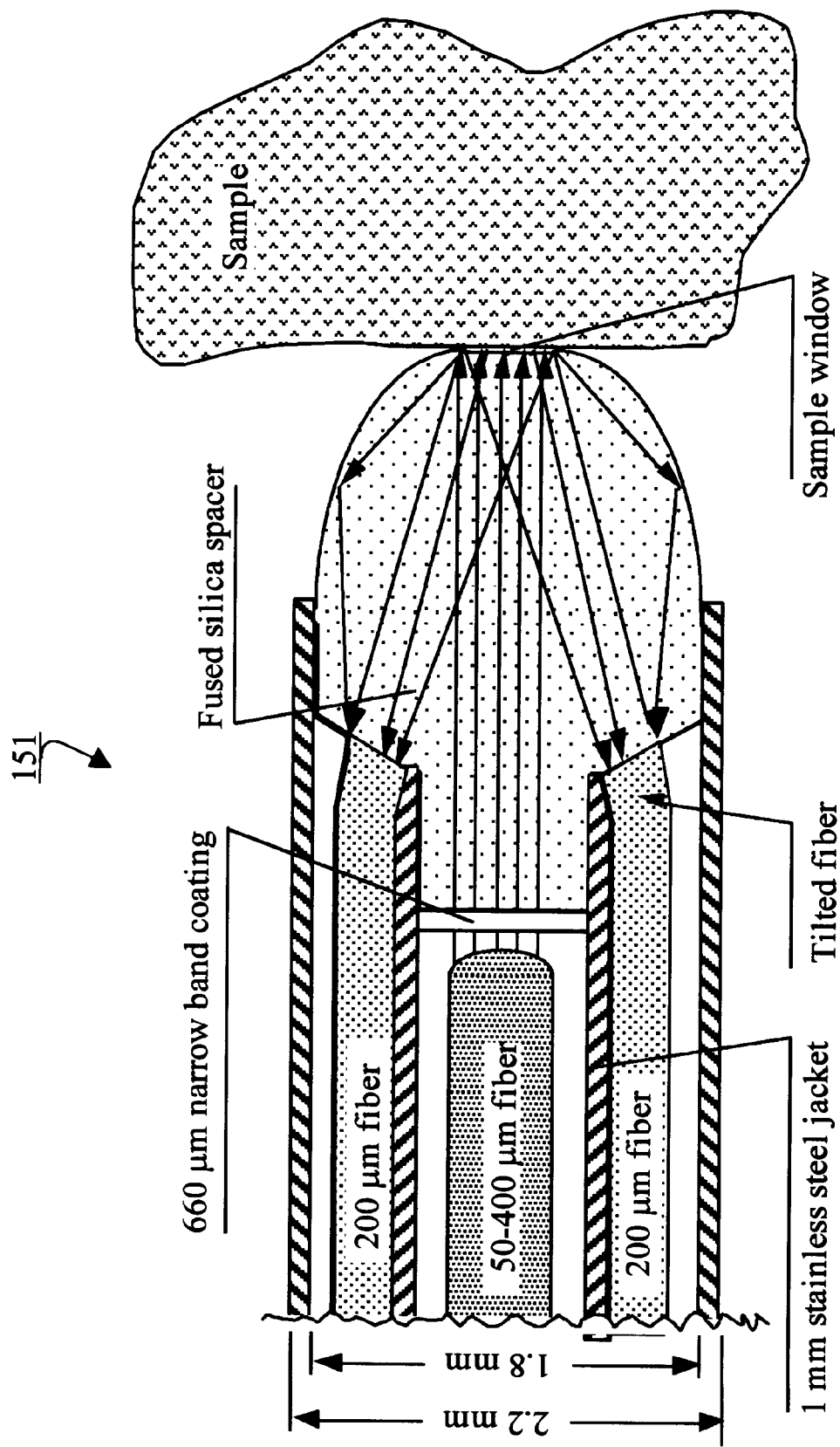
FIG. 15 is a fragmentary schematic longitudinal section view of a ninth embodiment of a fiberoptic assembly constructed according to the teachings of the present invention, the fiberoptic assembly being shown used to illuminate and collect light from a sample.
Figure 16:
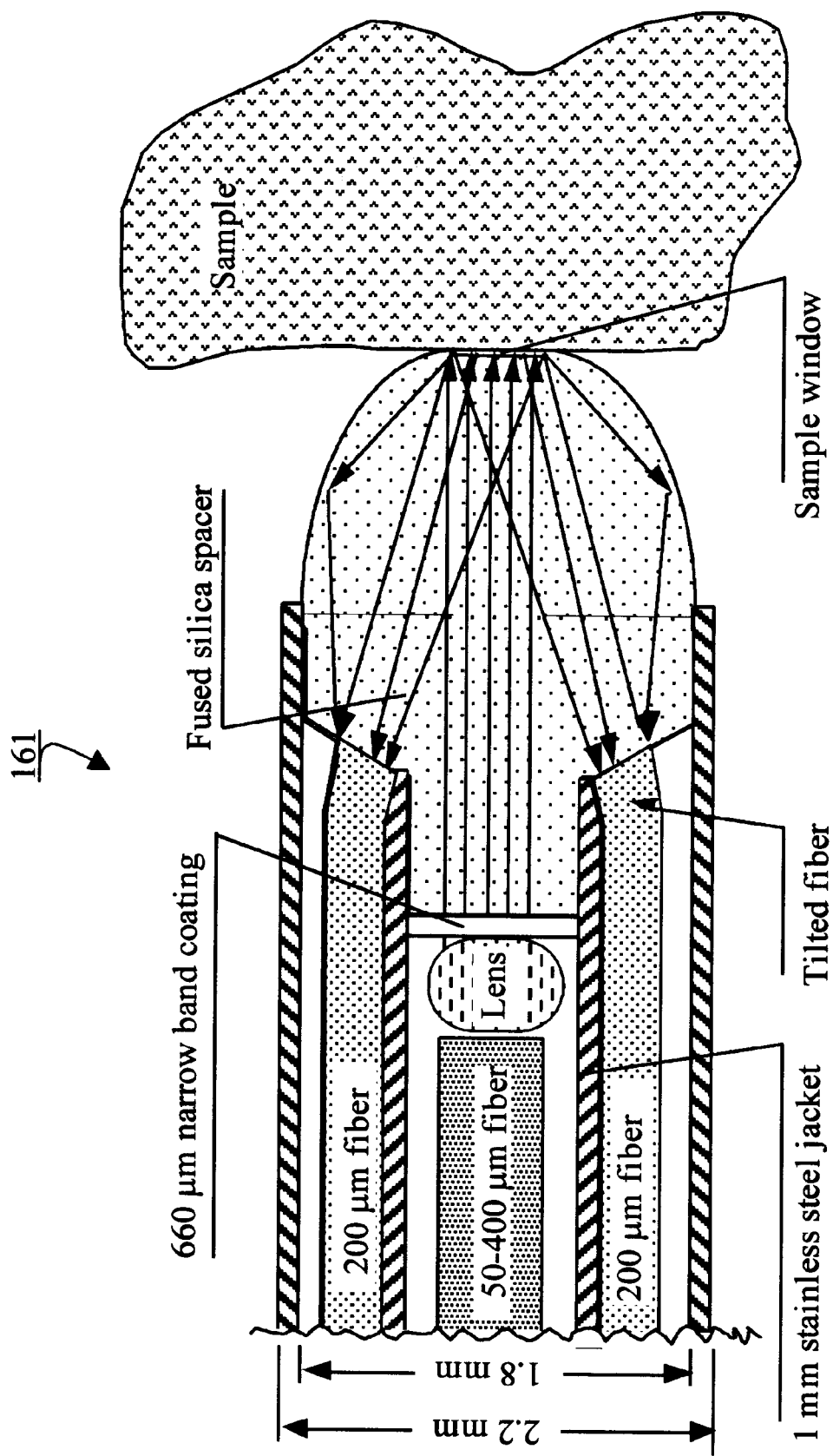
FIG. 16 is a fragmentary schematic longitudinal section view of a tenth embodiment of a fiberoptic assembly constructed according to the teachings of the present invention, the fiberoptic assembly being shown used to illuminate and collect light from a sample.
Figure 17:
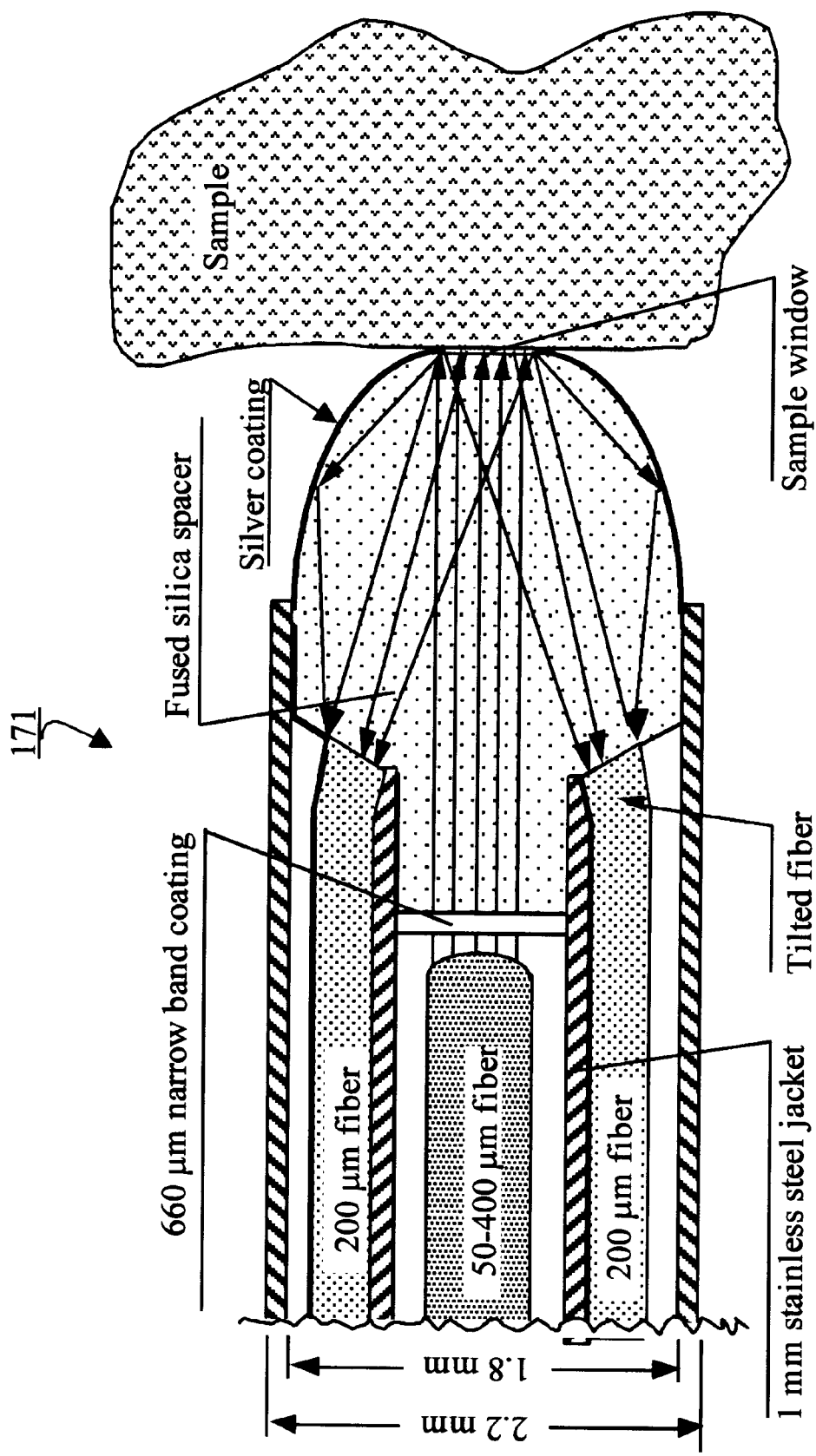
FIG. 17 is a fragmentary schematic longitudinal section view of a eleventh embodiment of a fiberoptic assembly constructed according to the teachings of the present invention, the fiberoptic assembly being shown used to illuminate and collect light from a sample.
Figure 18:
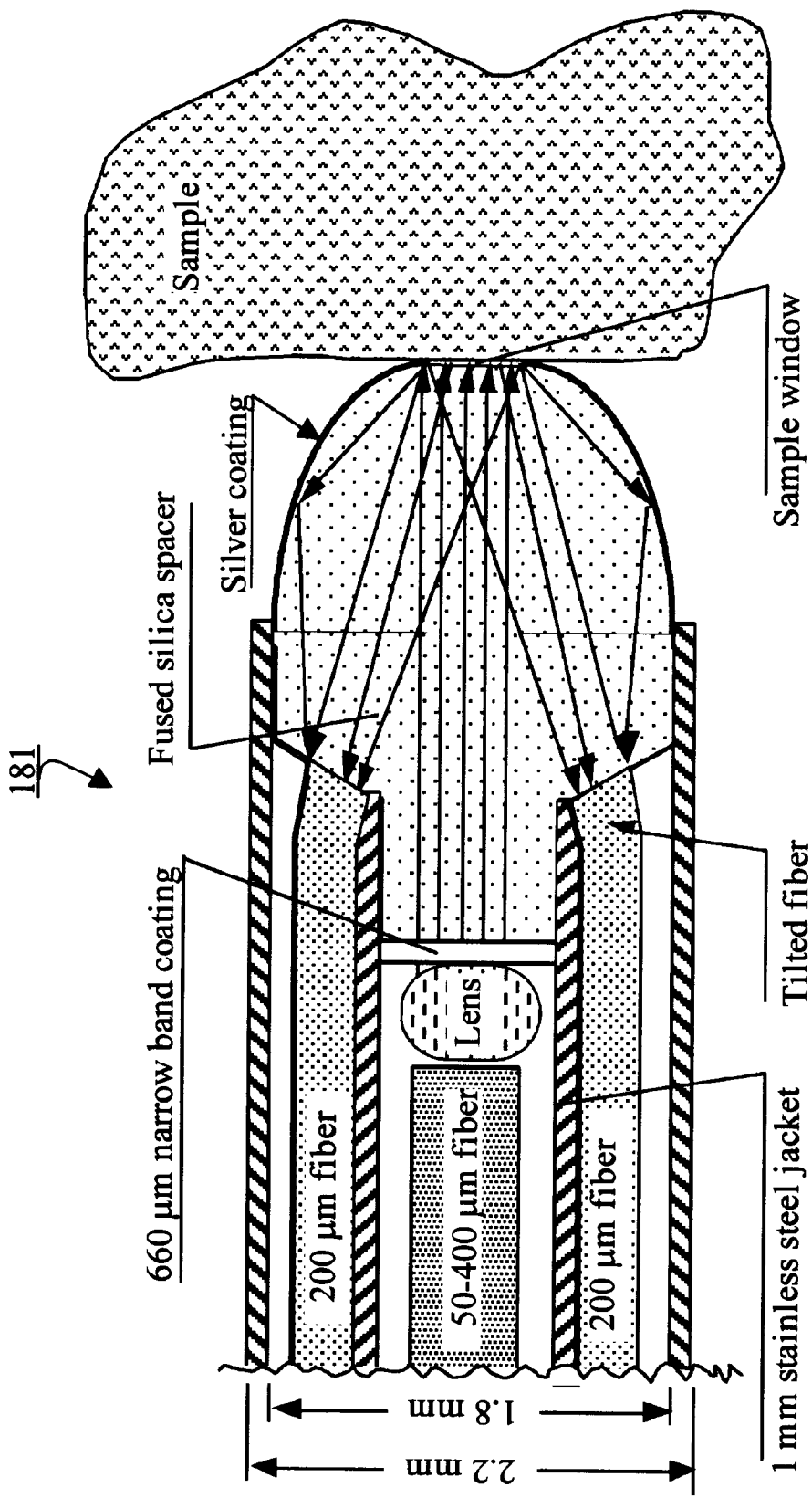
FIG. 18 is a fragmentary schematic longitudinal section view of a twelfth embodiment of a fiberoptic assembly constructed according to the teachings of the present invention, the fiberoptic assembly being shown used to illuminate and collect light from a sample.

A reflective coating (e.g., silver) can be applied to the outside surface of a parabolic spacer to reflect photons towards the light-collection fibers. Referring now to FIGS. 11 and 12, there are shown assemblies 111 and 121, respectively, assemblies 111 and 121 being identical to assemblies 91 and 101, respectively, except that assemblies 111 and 121 have spacers 113 and 123, respectively, the outsides of which are coated with a silver coating. In this way, the collection efficiency is increased since the collection angle is practically increase two-fold, and the exposure time needed to record a good-quality Raman spectrum from the sample is reduced.

Figure 19:
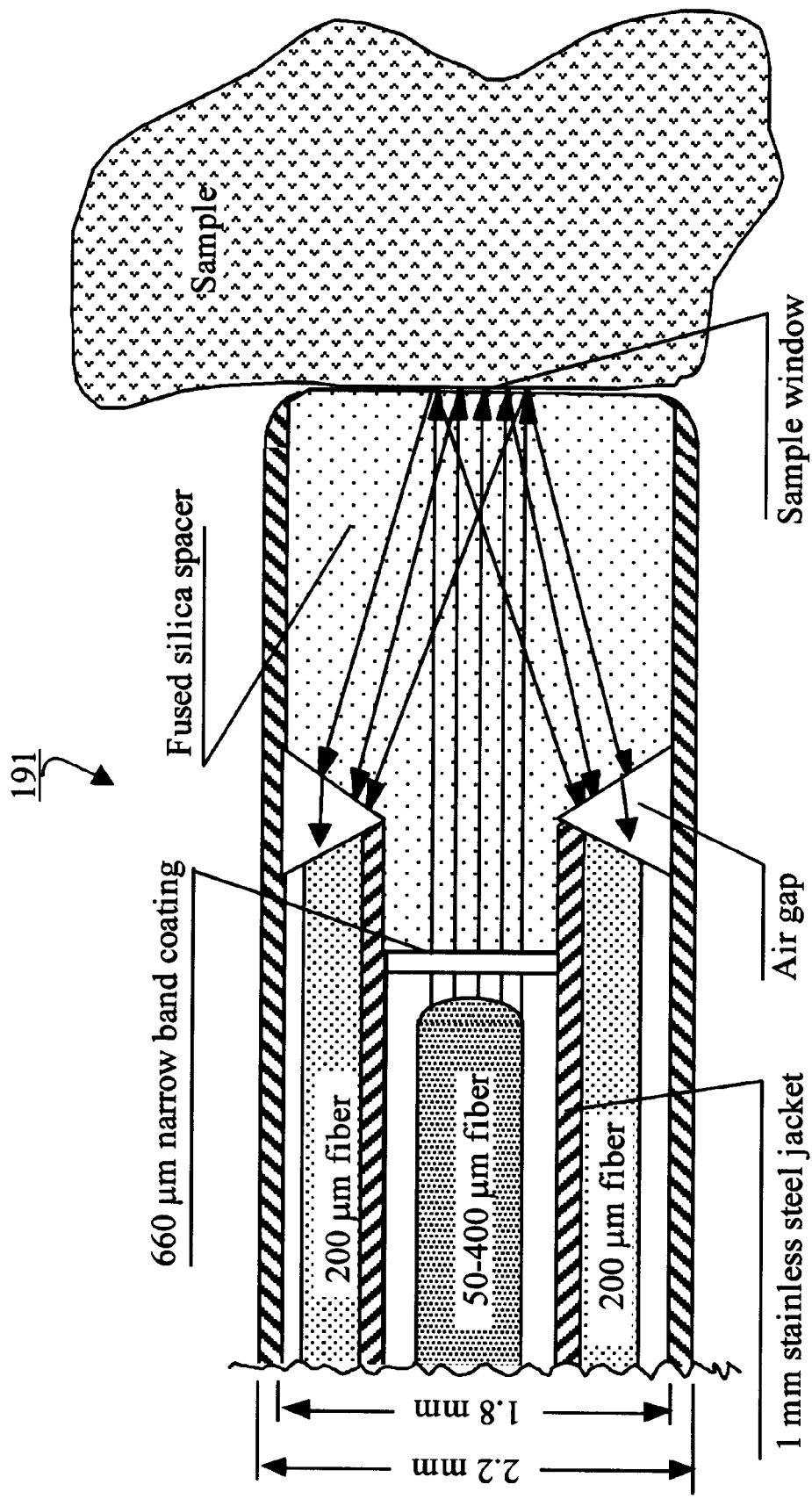
FIG. 19 is a fragmentary schematic longitudinal section view of a thirteenth embodiment of a fiberoptic assembly constructed according to the teachings of the present invention, the fiberoptic assembly being shown used to illuminate and collect light from a sample.
Figure 20:
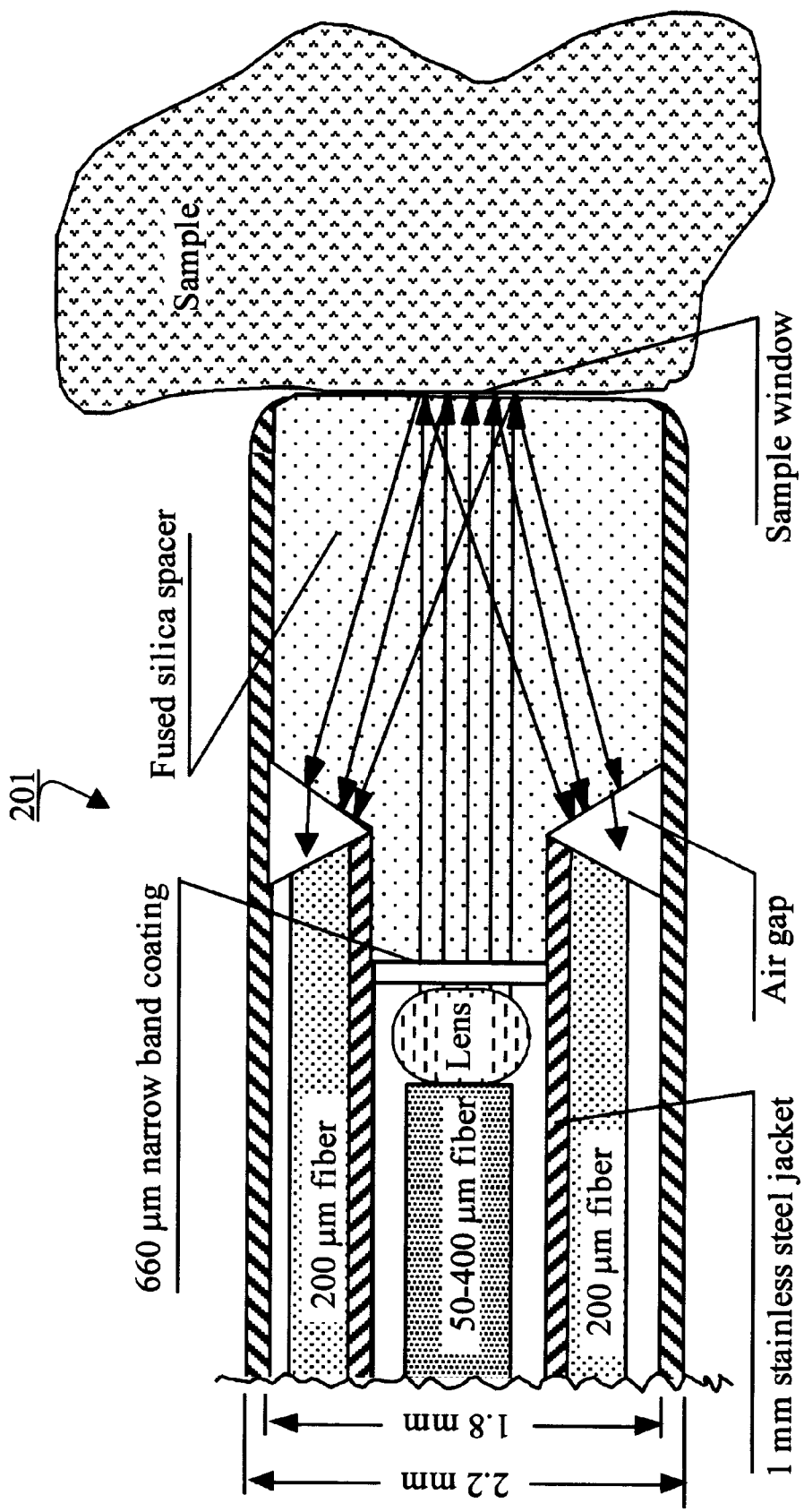
FIG. 20 is a fragmentary schematic longitudinal section view of a fourteenth embodiment of a fiberoptic assembly constructed according to the teachings of the present invention, the fiberoptic assembly being shown used to illuminate and collect light from a sample.

To improve light collection efficiency, the collection fibers can be aligned in a number of ways. In general, for maximum coupling efficiency, the photons from the sample should enter the collection fibers at approximately a 90 degree angle relative to the ends of the fibers. Referring now to FIGS. 13 through 18, there are shown assemblies 131, 141, 151, 161, 171 and 181, respectively. Assemblies 131, 141, 151, 161, 171 and 181 are similar to assemblies 21, 81, 91, 101, 111 and 121, respectively, the principal differences between the respective assemblies being that, in each of assemblies 131, 141, 151, 161, 171 and 181, the front ends of the collection fibers and those portions of the plugs in contact therewith are angled so that the front planes of the collection fibers are perpendicular to the direction of flight of the light from the sample. An alternative approach to that shown in FIGS. 13 through 18 is shown in FIGS. 19 and 20 wherein assemblies 191 and 201, respectively, are provided, assemblies 191 and 201 each having a triangular (in cross section) air gap between its spacer and its collection fibers. This air gap causes a change in the direction of flight of the light from the sample so that the light enters the collection fibers at approximately right angles thereto.

Figure 21:
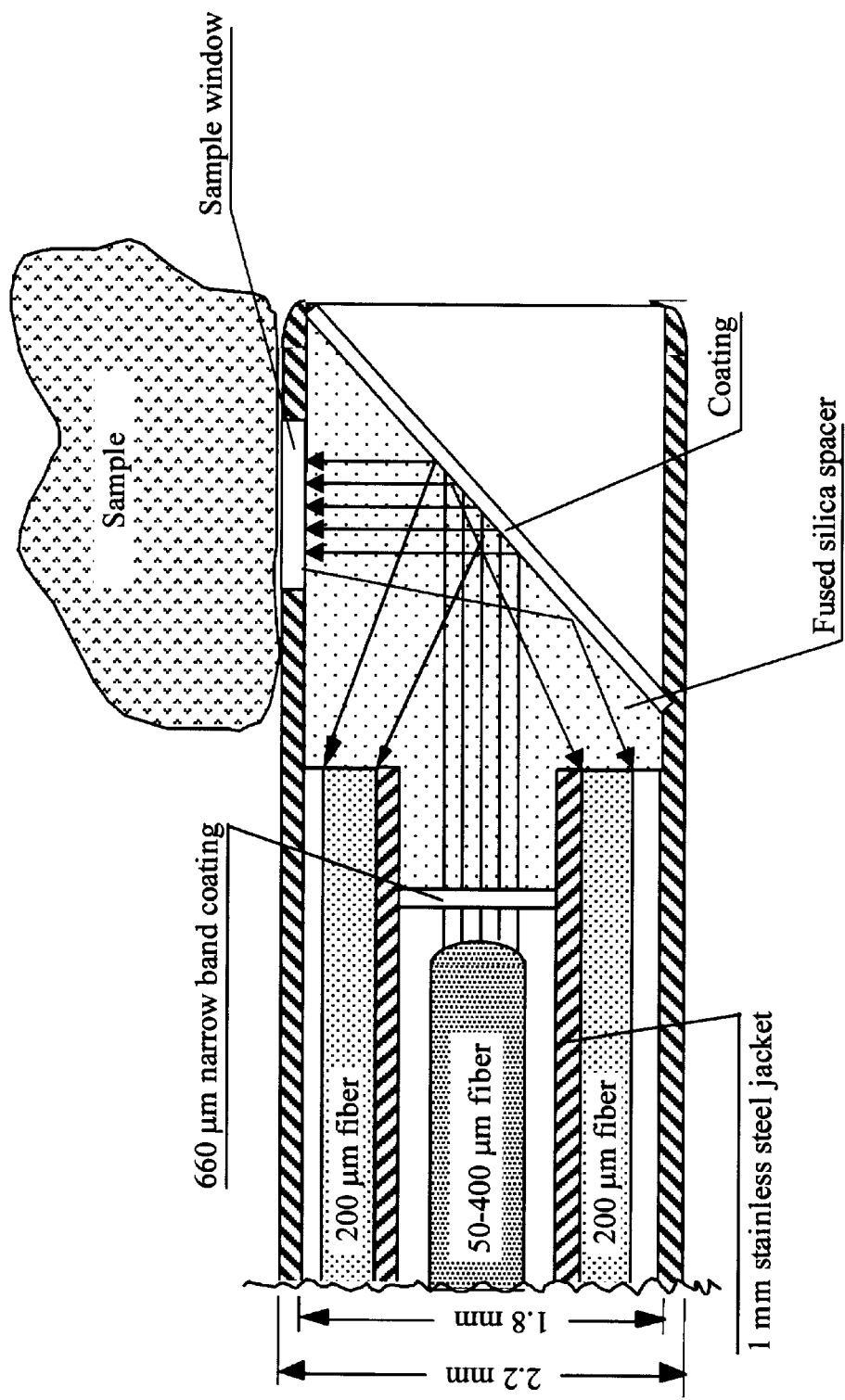
FIG. 21 is a fragmentary schematic longitudinal section view of a fifteenth embodiment of a fiberoptic assembly constructed according to the teachings of the present invention, the fiberoptic assembly being shown used to illuminate and collect light from a sample.
Figure 22:
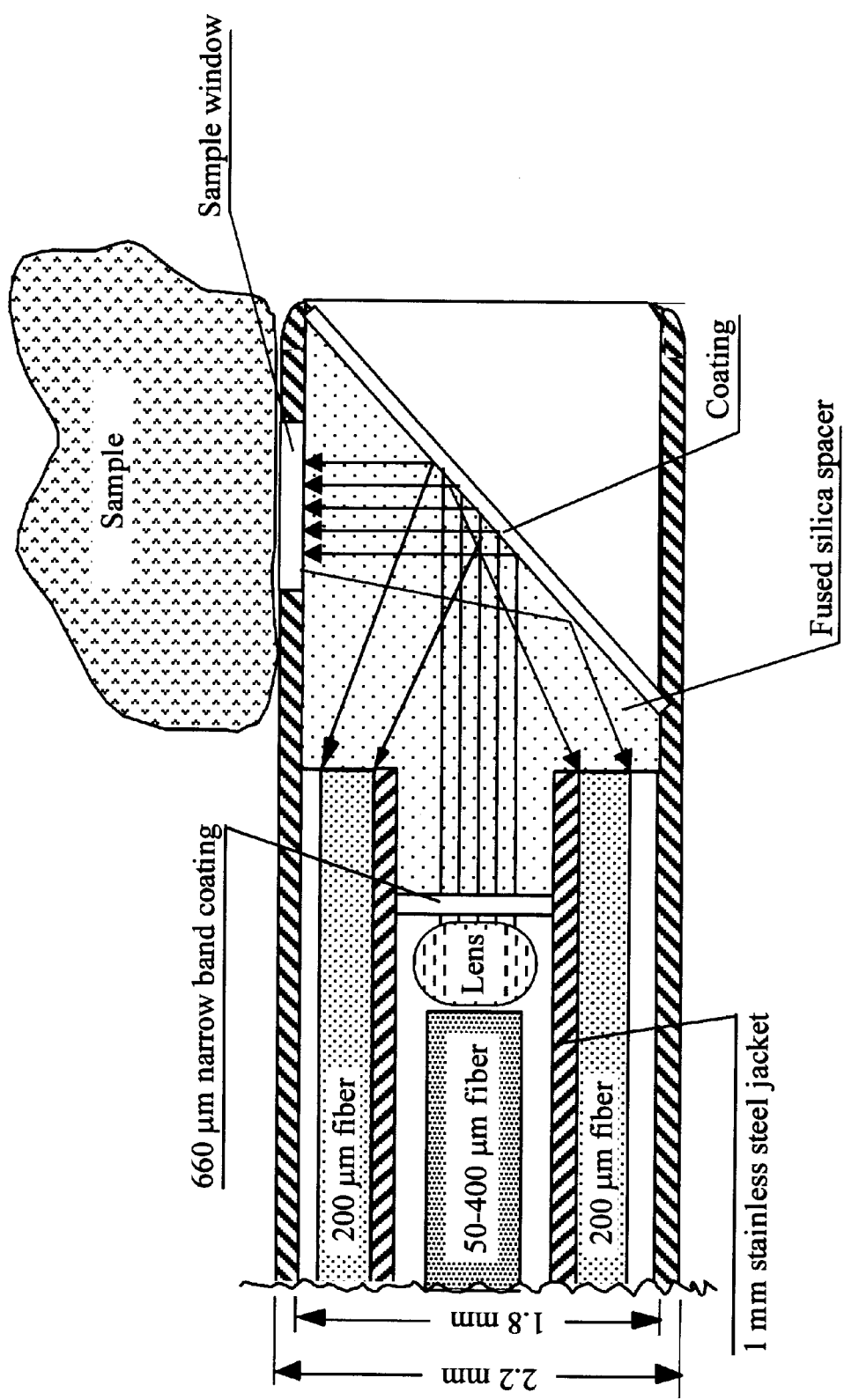
FIG. 22 is a fragmentary schematic longitudinal section view of a sixteenth embodiment of a fiberoptic assembly constructed according to the teachings of the present invention, the fiberoptic assembly being shown used to illuminate and collect light from a sample.
Figure 23:
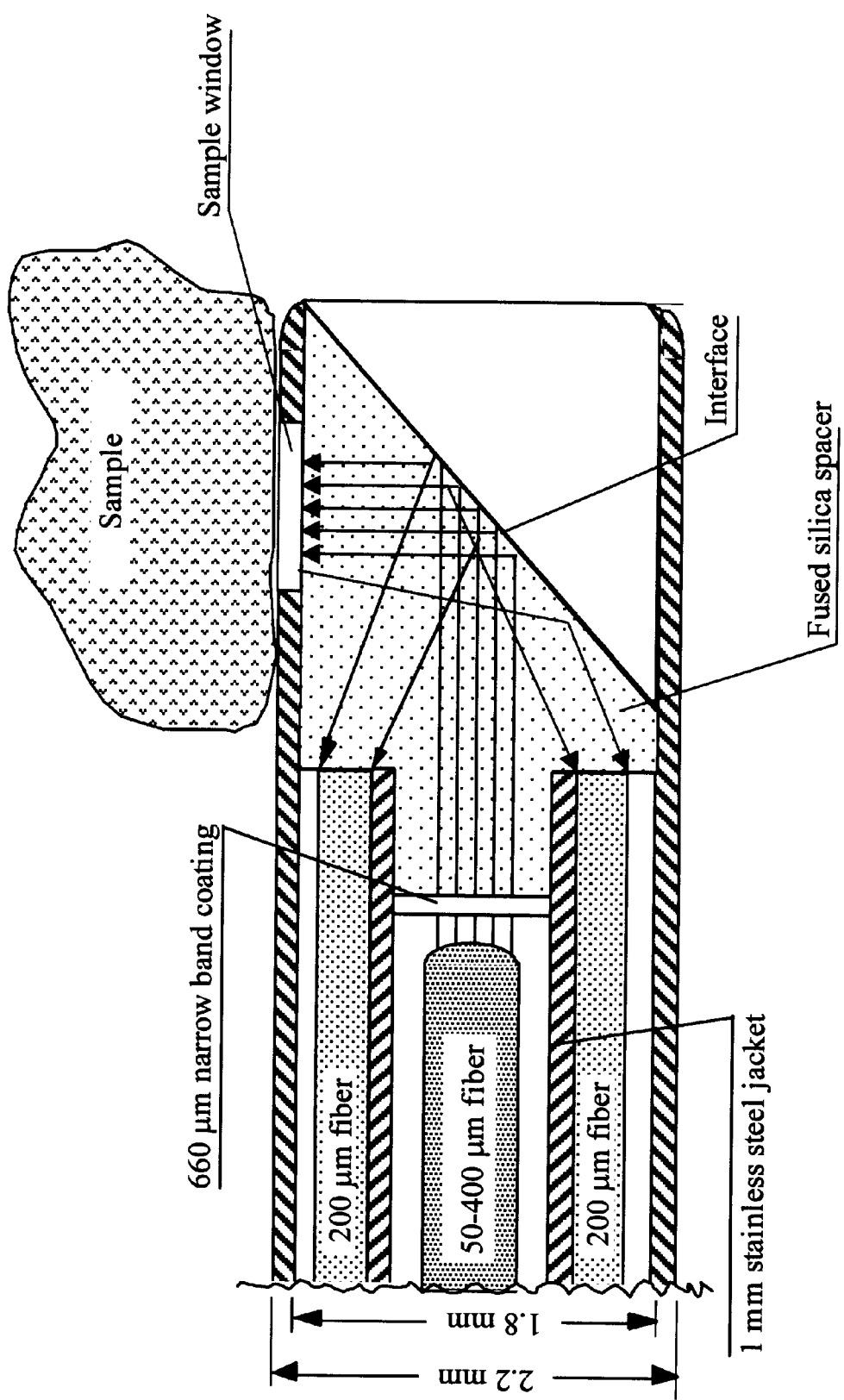
FIG. 23 is a fragmentary schematic longitudinal section view of a seventeenth embodiment of a fiberoptic assembly constructed according to the teachings of the present invention, the fiberoptic assembly being shown used to illuminate and collect light from a sample.
Figure 24:
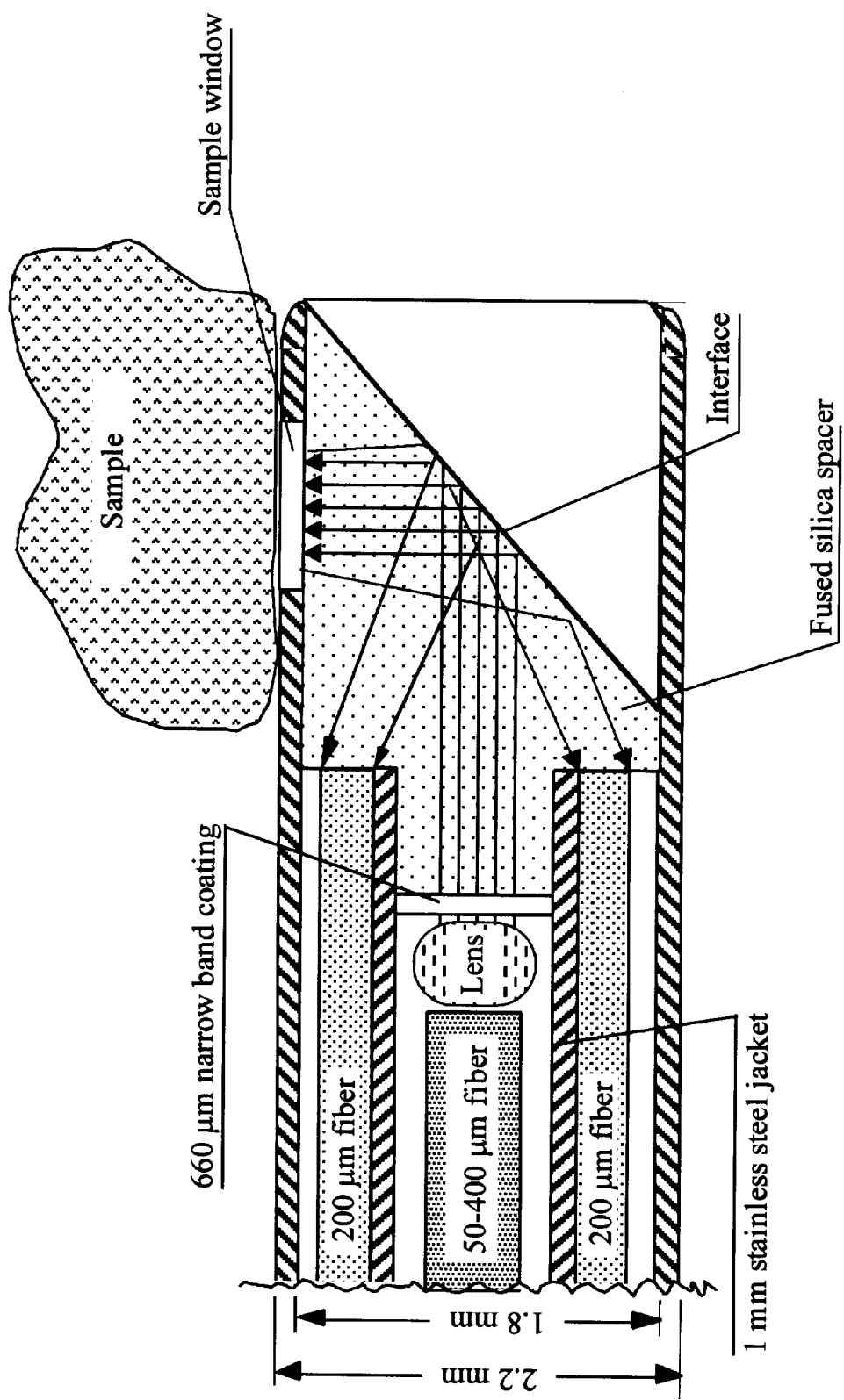
FIG. 24 is a fragmentary schematic longitudinal section view of an eighteenth embodiment of a fiberoptic assembly constructed according to the teachings of the present invention, the fiberoptic assembly being shown used to illuminate and collect light from a sample.
Figure 25:
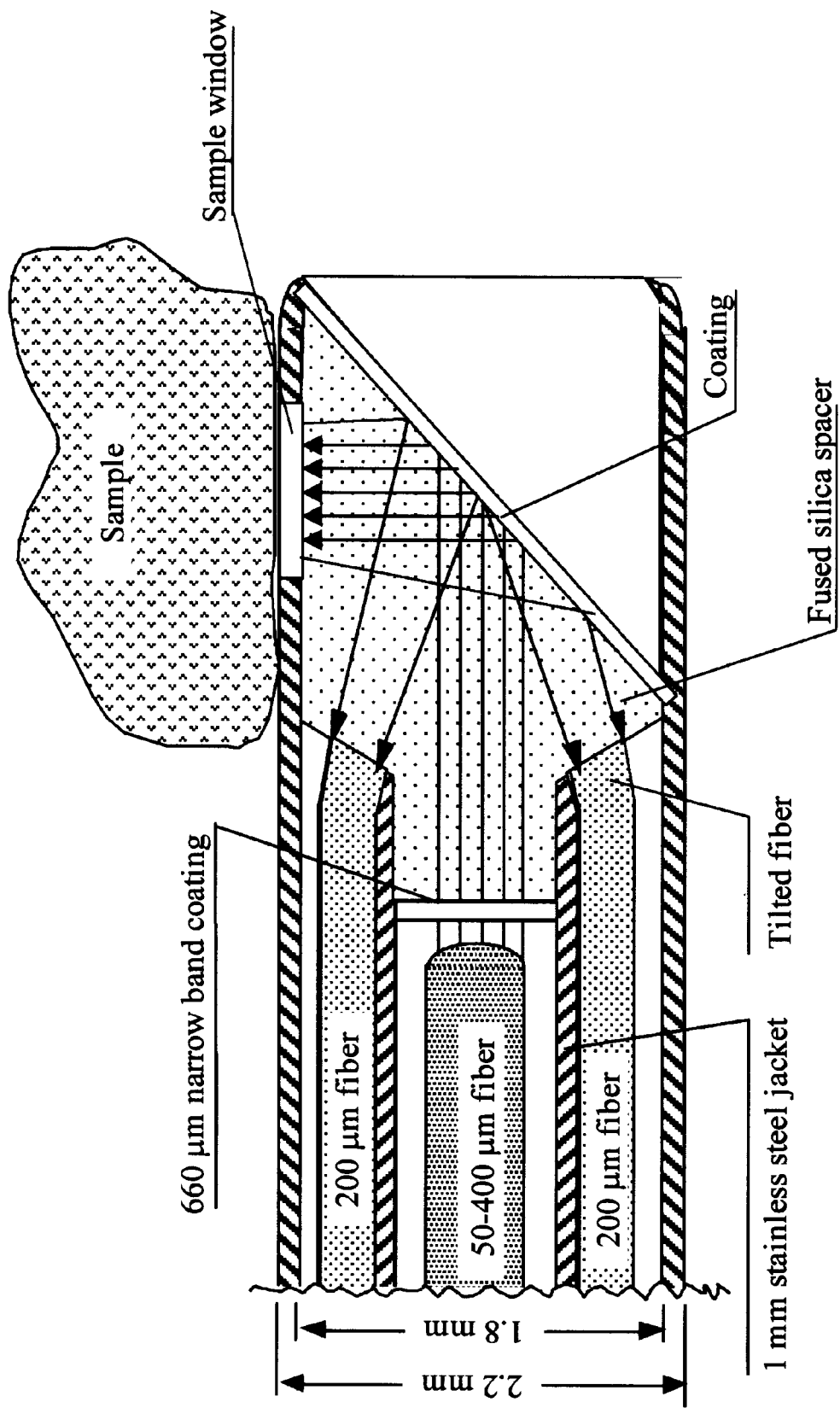
FIG. 25 is a fragmentary schematic longitudinal section view of a nineteenth embodiment of a fiberoptic assembly constructed according to the teachings of the present invention, the fiberoptic assembly being shown used to illuminate and collect light from a sample.
Figure 26:
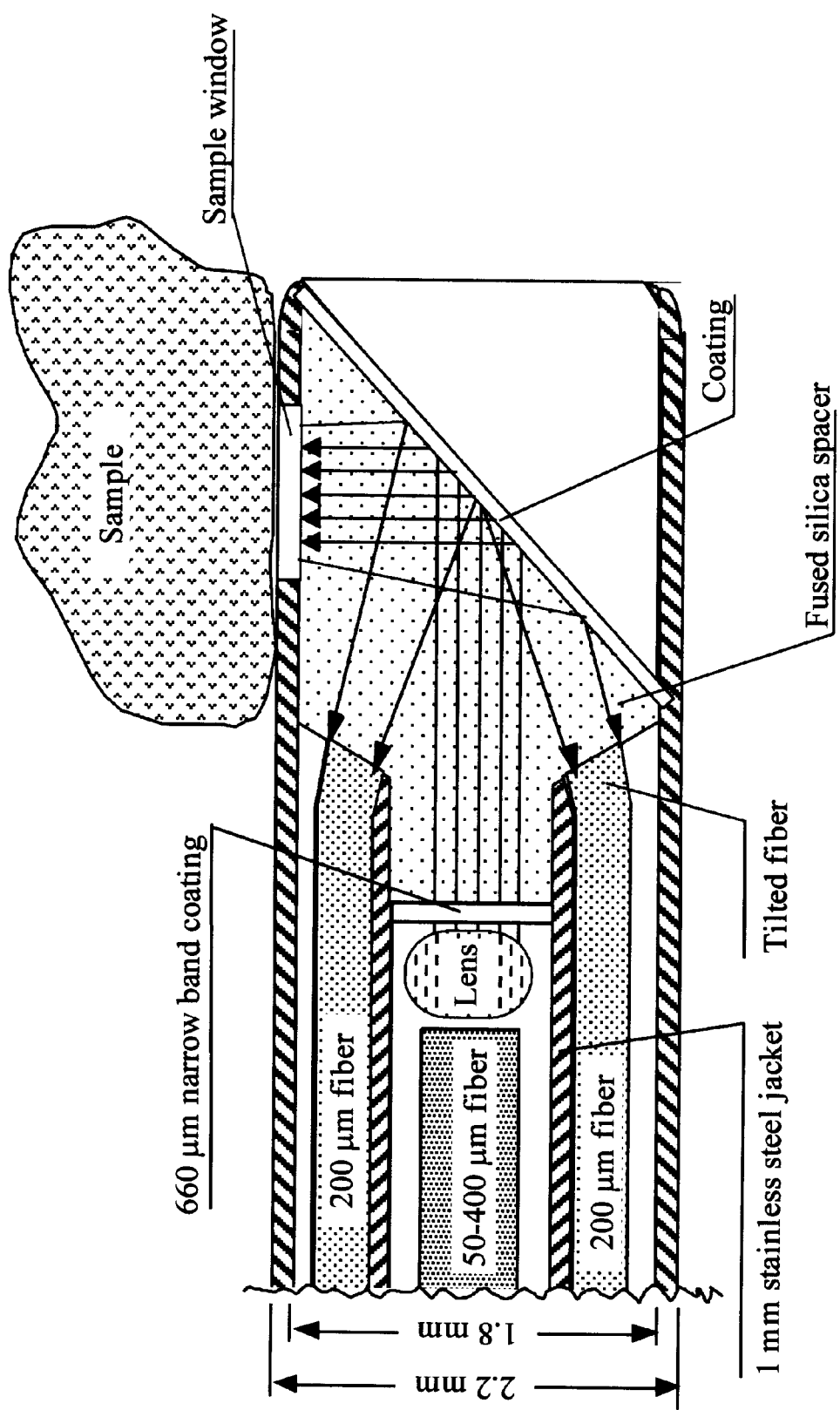
FIG. 26 is a fragmentary schematic longitudinal section view of a twentieth embodiment of a fiberoptic assembly constructed according to the teachings of the present invention, the fiberoptic assembly being shown used to illuminate and collect light from a sample.
Figure 27:
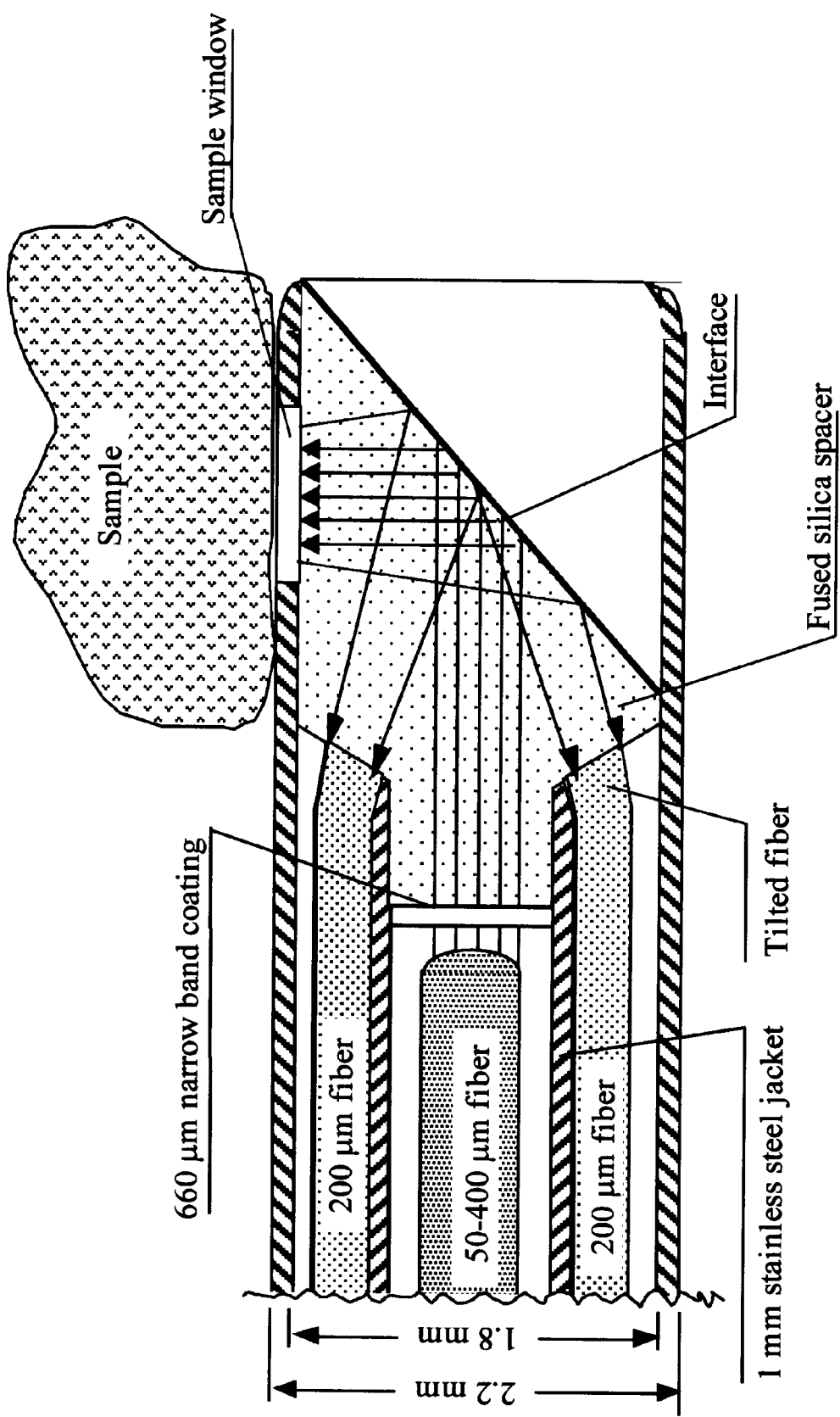
FIG. 27 is a fragmentary schematic longitudinal section view of a twenty-first embodiment of a fiberoptic assembly constructed according to the teachings of the present invention, the fiberoptic assembly being shown used to illuminate and collect light from a sample.
Figure 28:
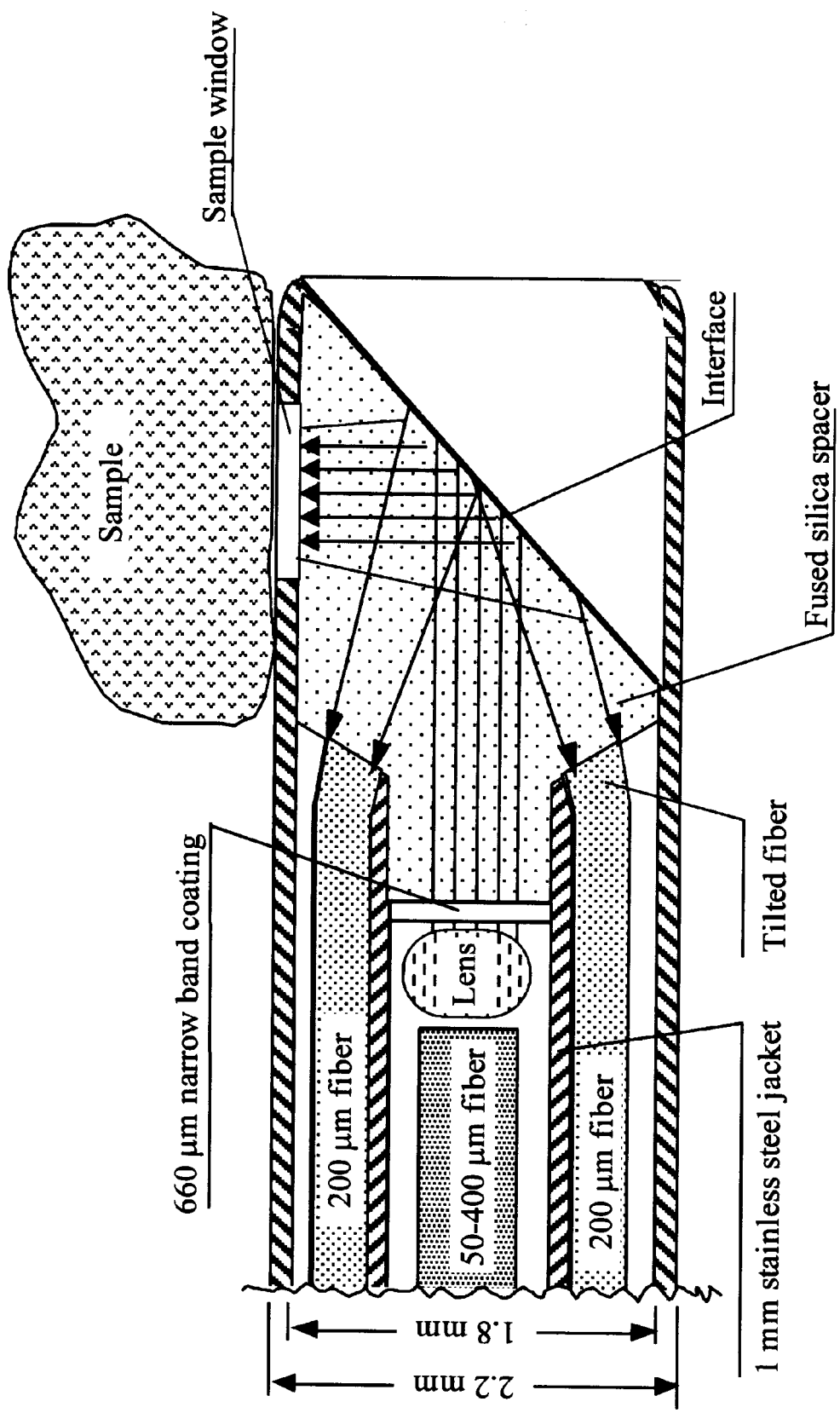
FIG. 28 is a fragmentary schematic longitudinal section view of a twenty-second embodiment of a fiberoptic assembly constructed according to the teachings of the present invention, the fiberoptic assembly being shown used to illuminate and collect light from a sample.

As can readily be appreciated, the sample under study may be located to the side of the fiber assembly, as opposed to in front of the fiber assembly. For this reason, in other embodiments of the invention, the fiber assembly is adapted for 90° side view collection. This is done by having a window in the side of the outer jacket and a 45° reflecting surface in the plug that directs light to and from the sample through the window. This reflecting surface is coated (dielectric or metal coating as shown in FIGS. 21 and 22) or acts as an interface between sections with different indices of refraction (for example quartz and an air gap as shown in FIGS. 23 and 24) to reflect the illuminating light in the direction of the sample. Alternative designs are shown in FIGS. 25 through 28 where the collection fibers are tilted for optimal light collection performance.

Figure 29:
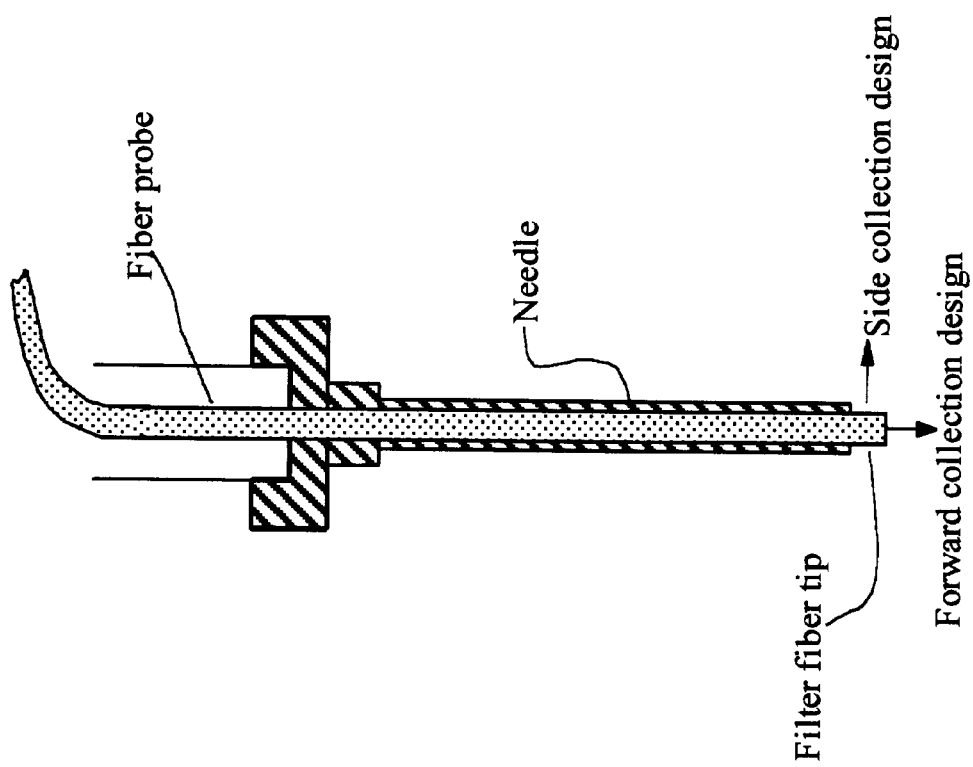
FIG. 29 is a fragmentary schematic longitudinal view of a first embodiment of a fiberoptic assembly including a needle constructed according to the teachings of the present invention.

The fiberoptic assembly of the present invention can also be used with a needle for minimally invasive in vivo measurements. One such arrangement is shown in FIG. 29. Either of the forward-collection-type or 90°-degree-collection-type assemblies described above can be used in connection with a needle for the spectroscopic analysis of the sample. As mentioned above, the size of the fiber assembly can be modified to meet the needs of the particular application. For example, one would use a fiber assembly with a small diameter with a needle to minimize the size of the needle.

Figure 30:
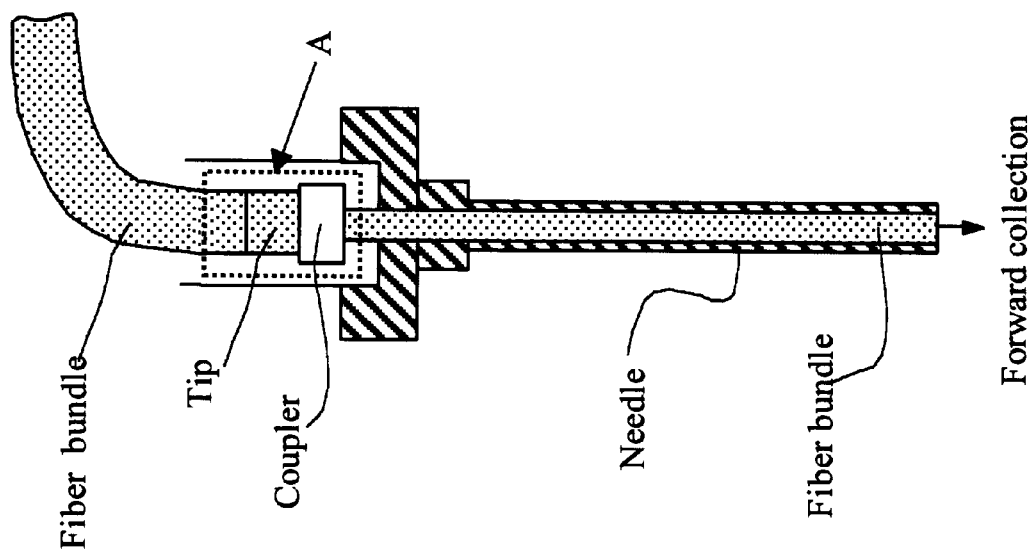
FIG. 30 is a fragmentary schematic longitudinal section view of a second embodiment of a fiberoptic assembly including a needle constructed according to the teachings of the present invention.
Figure 31:
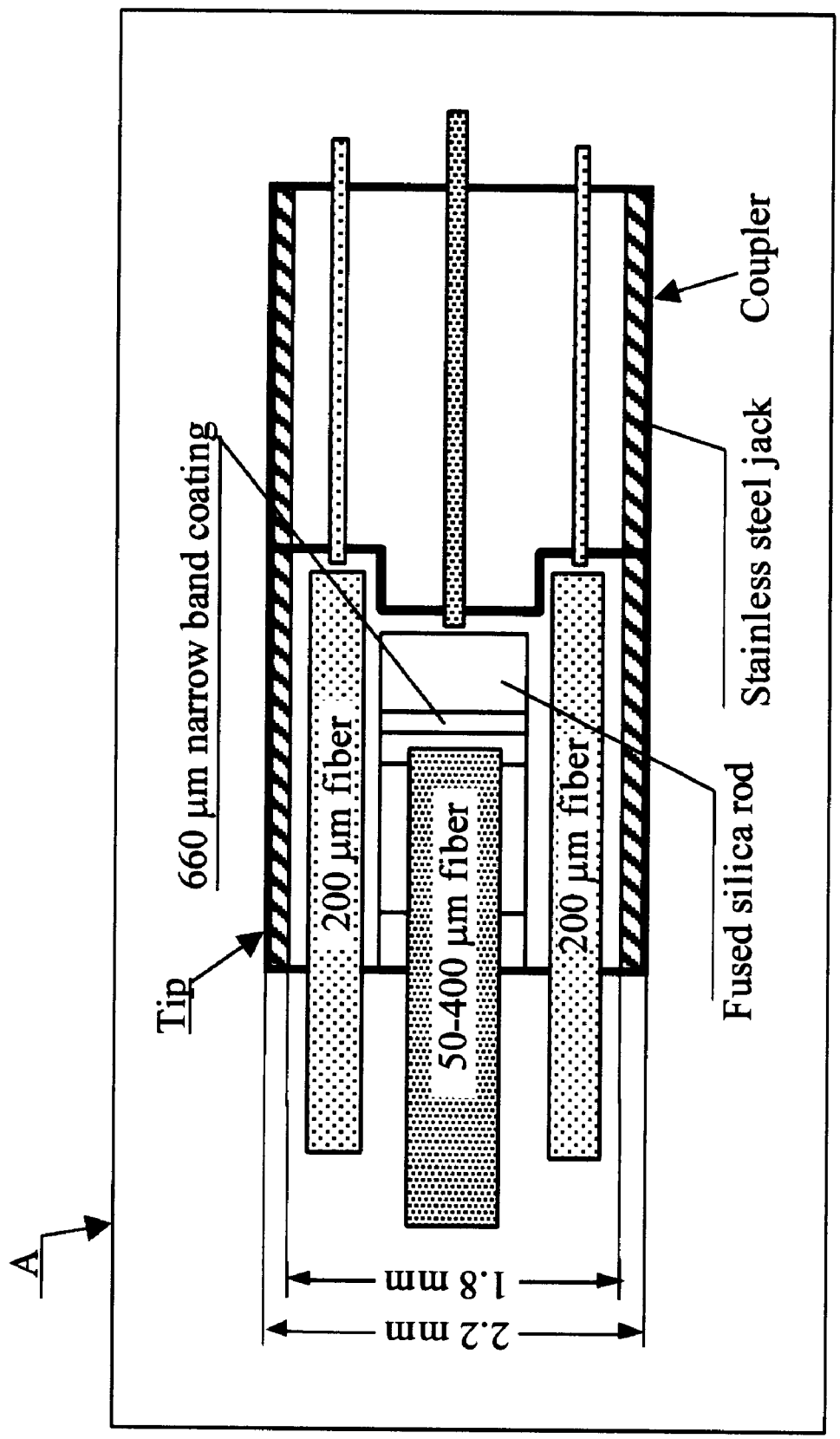
FIG. 31 is an enlarged fragmentary schematic longitudinal section view showing area A of FIG. 30 in greater detail.

An alternative embodiment of a fiber assembly for use with a needle is shown in FIGS. 30 and 31. In this embodiment, the spacer or plug of previously described embodiments is replaced with a fused silica rod positioned just beyond the end of the illuminating fiber, the fused silica rod having the narrow band filter attached thereto. This fiber assembly is coupled just before the needle to a fiber system comprising fiber elements having cross-sectional diameters small enough to fit into the opening of the needle and lengths long enough to pass through the needle.

Figure 32A:
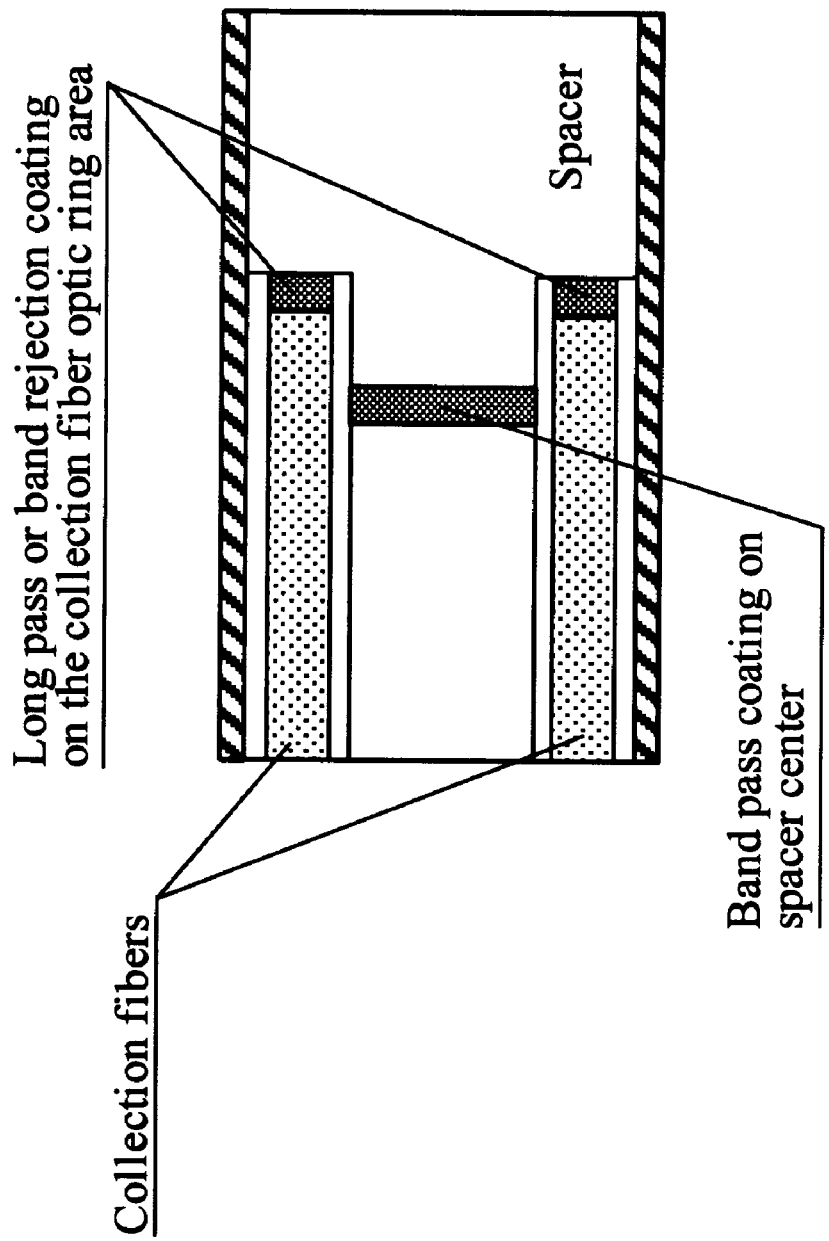
FIGS. 32(*a*) through 32(*c*) are fragmentary schematic longitudinal section views of three additional embodiments of a fiberoptic assembly constructed according to the teachings of the present invention.
Figure 32B:
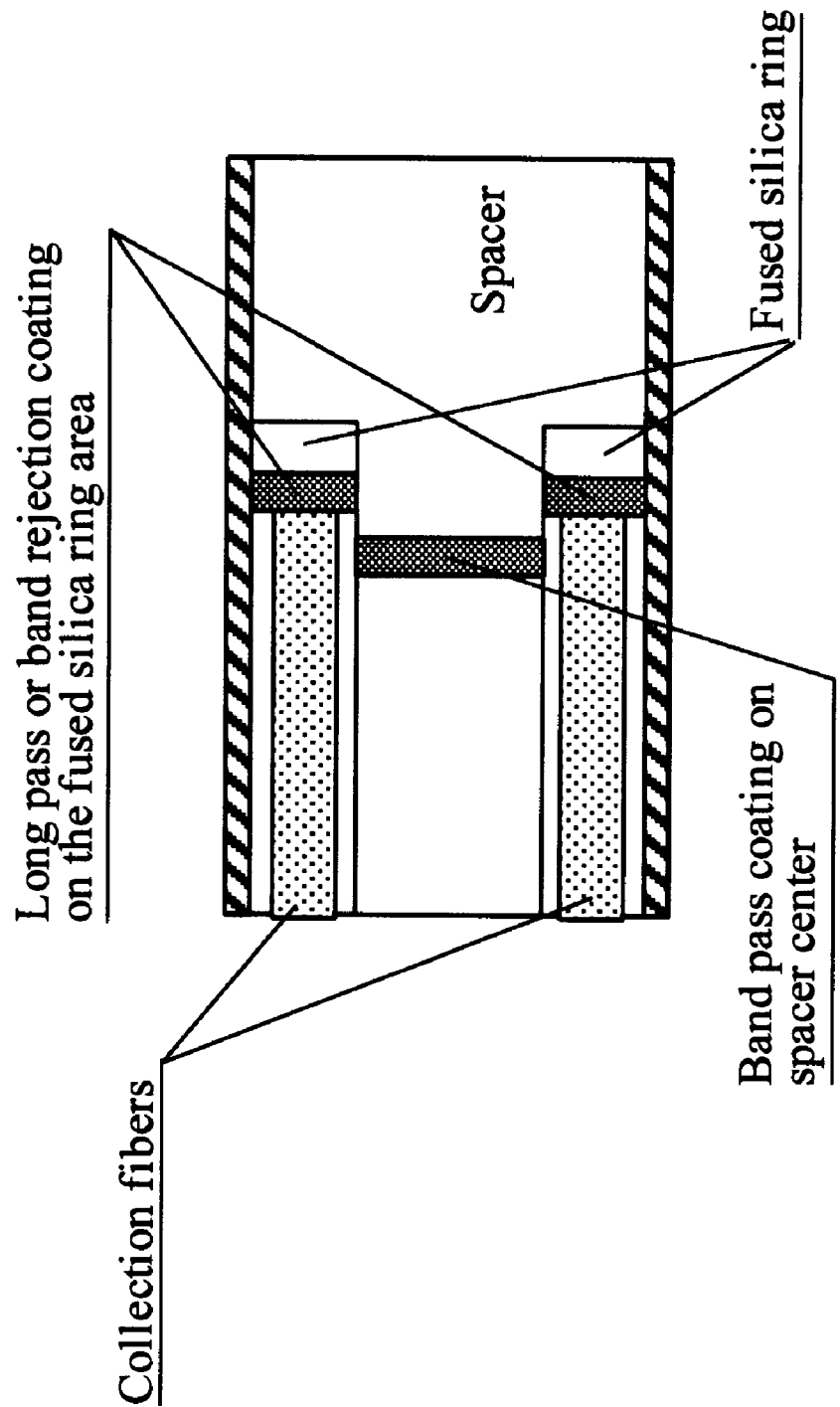
Figure 32C:
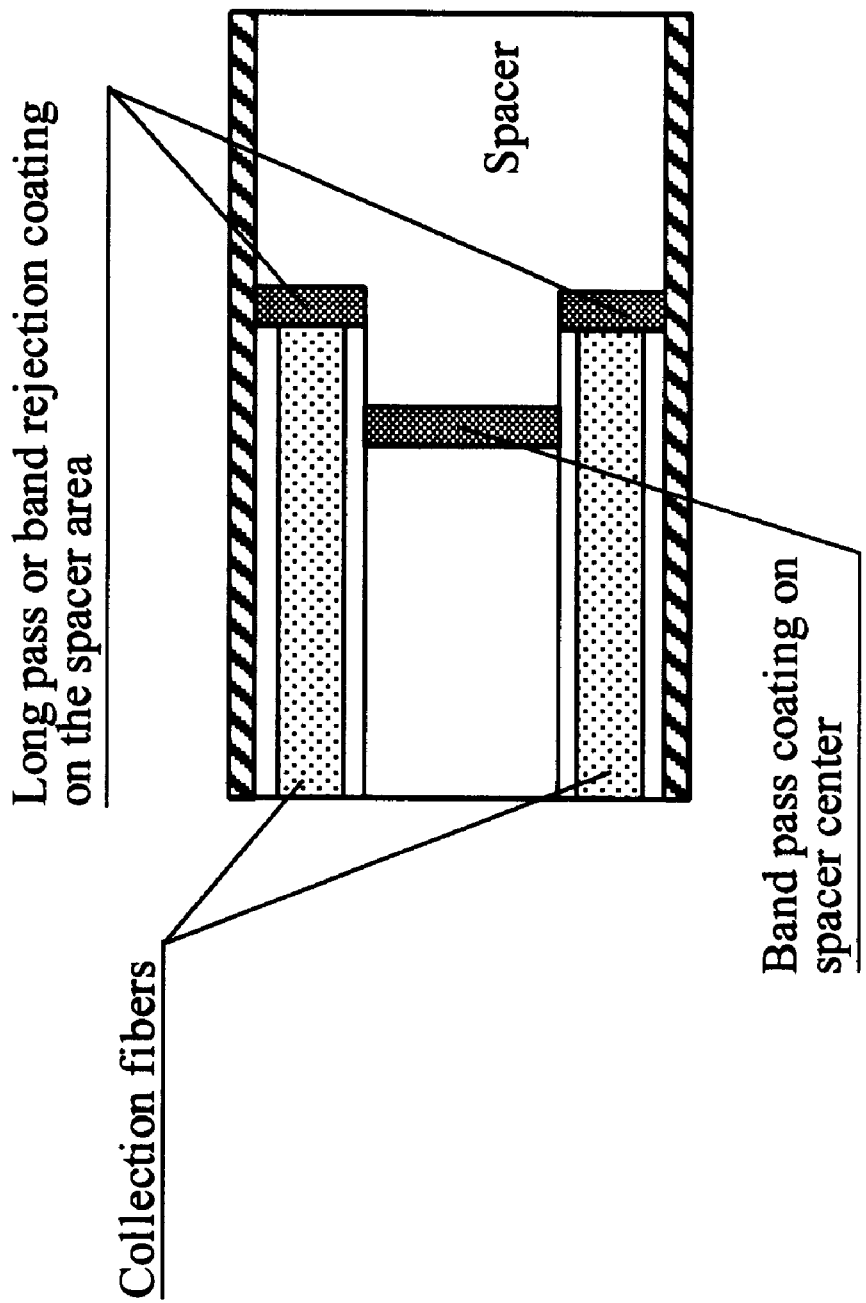

Referring now to FIGS. 32(a) and 32(c), there are shown three additional embodiments of a fiberoptic assembly constructed according to teachings of the present invention. These three embodiments include different types of long pass filter or band rejection filter means on the front of the collection fibers to block out any excitation laser light back scattered from a sample. In FIG. 32(a), the filter coating is applied directly to the collection fiber input surface. In FIG. 32(b), a small fused silica disc ring is located between the collection fibers and the plug, with the long pass or band rejection filter coating applied to said fused silica disc ring. In FIG. 32(c), the filter coating is applied to the rear end surface of the plug aligned with the collection fibers.

The embodiments of the present invention recited herein are intended to be merely exemplary and those skilled in the art will be able to make numerous variations and modifications to it without departing from the spirit of the present invention. All such variations and modifications are intended to be within the scope of the present invention as defined by the claims appended hereto.

What is claimed is:

1. A fiberoptic assembly comprising:
   (a) an illumination fiber, said illumination fiber having an output end;
   (b) a first light collection fiber, said first light collection fiber having an input end;
   (c) a tubular jacket, at least said output end of said illumination fiber and at least said input end of said first light collection fiber being disposed within said tubular jacket; and
   (d) a narrow band filter, said narrow band filter being aligned with and positioned after said output end of said illumination fiber and having a cross-sectional area no larger than that of said tubular jacket.

2. The fiberoptic assembly as claimed in claim 1 wherein said narrow band filter is disposed within said tubular jacket.

3. The fiberoptic assembly as claimed in claim 2 wherein said tubular jacket has an open front end, said fiberoptic assembly further comprising a plug disposed within said open front end of said tubular jacket.

4. The fiberoptic assembly as claimed in claim 3 wherein said narrow band filter is a coating applied to the rear of said plug.

5. The fiberoptic assembly as claimed in claim 3 wherein said plug has a parabolic-shaped front end.

6. The fiberoptic assembly as claimed in claim 1 wherein said tubular jacket has an outer diameter of no more than 3 mm.

7. The fiberoptic assembly as claimed in claim 1 further comprising a second light collection fiber, said second light collection fiber having an input end, at least said input end of second light collection fiber being disposed within said tubular jacket.

8. The fiberoptic assembly as claimed in claim 1 further comprising a filter disposed in front of said input end of said first light collection fiber.

9. The fiberoptic assembly as claimed in claim 1 further comprising a lens disposed within said jacket after said output end of said illumination fiber for collimating light emergent from said illumination fiber.

10. The fiberoptic assembly as claimed in claim 1 wherein said output end of said illumination fiber is shaped to collimate light emergent from said illumination fiber.

11. The fiberoptic assembly as claimed in claim 1 further comprising a hollow needle, said tubular jacket being disposed within said hollow needle.

12. The fiberoptic assembly as claimed in claim 3 wherein said tubular jacket is provided with a side opening and wherein said plug has a reflective surface for directing light from said illumination fiber through said side opening and through said side opening to said first light collection fiber.

13. The fiberoptic assembly as claimed in claim 3 further comprising a rod disposed within said tubular jacket between said illumination fiber and said plug, said narrow band filter being mounted on said rod.

14. The fiberoptic assembly as claimed in claim 3 wherein said plug is made of fused silica.

15. The fiberoptic assembly as claimed in claim 1 wherein said illumination fiber has a cross-sectional diameter of about 50–400 $\mu$m, said first light collection fiber has a cross-sectional diameter of about 200 $\mu$m and said narrow band filter has a cross-sectional diameter of about 660 $\mu$m.

16. The fiberoptic assembly as claimed in claim 1 wherein said tubular jacket is made of stainless steel.

17. The fiberoptic assembly as claimed in claim 5 further comprising a layer of silver applied to said front end of said plug.

18. A fiberoptic assembly comprising:
   (a) an illumination fiber, said illumination fiber having an output end;
   (b) an inner tubular jacket, at least said output end of said illumination fiber being disposed within said inner tubular jacket;
   (c) an outer tubular jacket, said inner tubular jacket being coaxial with and disposed within said outer tubular jacket;
   (d) a plurality of light collection fibers, each of said light collection fibers having an input end, at least said output ends of said plurality of light collection fibers being disposed within said outer tubular jacket and spaced about the outside of said inner tubular jacket; and
   (e) a narrow band filter, said narrow band filter being aligned with and positioned after said output end of said illumination fiber and having a cross-sectional area no larger than that of said outer tubular jacket.

19. The fiberoptic assembly as claimed in claim 18 wherein said narrow band filter is disposed within said outer tubular jacket.

20. The fiberoptic assembly as claimed in claim 19 wherein said narrow band filter is disposed within said inner tubular jacket.

21. The fiberoptic assembly as claimed in claim 18 wherein said outer tubular jacket has an outer diameter of less than 3 mm.

22. The fiberoptic assembly as claimed in claim 18 wherein said outer tubular jacket has an open front end, said fiberoptic assembly further comprising a plug disposed within said open front end of said outer tubular jacket.

23. The fiberoptic assembly as claimed in claim 22 wherein said outer tubular jacket extends forwardly a short distance beyond said inner tubular jacket and wherein said plug comprises a front portion and a rear portion, said rear portion being situated in said inner tubular jacket, said front portion being situated in said outer tubular jacket and extending forwardly from said inner tubular jacket to at least said open front end of said outer tubular jacket.

24. The fiberoptic assembly as claimed in claim 23 wherein said input ends of said light collection fibers are angled radially inwardly towards said inner tubular jacket.

25. The fiberoptic assembly as claimed in claim 24 wherein the rear end of said front portion of said plug abuts said input ends of said light collection fibers.

26. The fiberoptic assembly as claimed in claim 23 wherein said input ends of said light collection fibers and the rear end of said front portion of said plug are appropriately shaped to jointly define a space of triangular cross-section.

27. A tip mountable on a fiberoptic bundle, the fiberoptic bundle comprising an illumination fiber and a light collection fiber, said tip comprising:
   (a) a first tubular jacket, said first tubular jacket being sized to receive at least the output end of the illumination fiber and at least the input end of the light collection fiber, said first tubular jacket having an outer diameter of less than 3 mm;
   (b) a narrow band filter disposed within said first tubular jacket.

28. The tip as claimed in claim 27 wherein said first tubular jacket has an open front end, said tip further comprising a plug disposed within said open front end of said first tubular jacket.

29. The tip as claimed in claim 28 wherein said narrow band filter is a coating applied to the rear of said plug.

30. The tip as claimed in claim 29 further comprising a second tubular jacket, said second tubular jacket being coaxial with said first tubular jacket and being disposed within said first tubular jacket, said narrow band filter being disposed within said second tubular jacket.

31. The fiberoptic assembly as claimed in claim 8 wherein said filter disposed in front of said input end of said first light collection fiber is a long pass filter for filtering out light passed through said narrow band filter and thereafter scattered.

32. The fiberoptic assembly as claimed in claim 31 wherein said long pass filter is in the form of a coating applied directly to said input end of said first light collection fiber.

33. The fiberoptic assembly as claimed in claim 31 wherein said long pass filter is in the form of a coating applied to a fused silica disc located in front of said input end of said first light collection fiber.

34. The fiberoptic assembly as claimed in claim 3 further comprising a long pass filter disposed in front of said input end of said first light collection fiber for filtering out light passed through said narrow band filter and thereafter scattered, said long pass filter being in the form of a coating applied to the rear of said plug.

35. The fiberoptic assembly as claimed in claim 18 further comprising a plurality of long pass filters, each of said long pass filters being disposed in front of the input end of one of said light collection fibers for blocking transmission to its corresponding light collection fiber of light passed through said narrow band filter and thereafter scattered.

36. The fiberoptic assembly as claimed in claim 35 wherein said long pass filters are disposed within said outer tubular jacket.

37. The fiberoptic assembly as claimed in claim 36 wherein said long pass filters are in the form of coatings applied to the respective input ends of the light collection fibers.

38. The fiberoptic assembly as claimed in claim 36 wherein said long pass filters are in the form of coatings, each of said coatings being applied to a fused silica disc located in front of the input end of one of said light collection fibers.

39. The fiberoptic assembly as claimed in claim 23 further comprising a plurality of long pass filters, each of said long pass filters being disposed in front of the input end of one of said light collection fibers for blocking transmission to its corresponding light collection fiber of light passed through said narrow band filter and thereafter scattered, said long pass filters being in the form of coatings applied directly to the rear end of the front portion of said plug.

* * * * *